US008444578B2

(12) United States Patent
Bourget et al.

(10) Patent No.: US 8,444,578 B2
(45) Date of Patent: May 21, 2013

(54) WEARABLE AMBULATORY DATA RECORDER

(75) Inventors: Duane L. Bourget, Albertville, MN (US); Keith A. Miesel, St. Paul, MN (US); Gregory F. Molnar, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/217,011

(22) Filed: Aug. 24, 2011

(65) Prior Publication Data

US 2011/0313261 A1 Dec. 22, 2011

Related U.S. Application Data

(63) Continuation of application No. 11/413,619, filed on Apr. 28, 2006, now Pat. No. 8,016,776.

(60) Provisional application No. 60/742,002, filed on Dec. 2, 2005, provisional application No. 60/785,657, filed on Mar. 24, 2006.

(51) Int. Cl.
*A61B 5/103* (2006.01)

(52) U.S. Cl.
USPC .......................................................... 600/595

(58) Field of Classification Search
USPC .......................................................... 600/595
See application file for complete search history.

(56) References Cited

U.S. PATENT DOCUMENTS

| 4,297,685 | A |   | 10/1981 | Brainard, II |
| 4,550,736 | A |   | 11/1985 | Broughton et al. |
| 4,771,780 | A |   | 9/1988  | Sholder |
| 4,776,345 | A |   | 10/1988 | Cohen et al. |
| 4,846,195 | A |   | 7/1989  | Alt |
| 4,859,203 | A | * | 8/1989  | Eckhaus ........................ 439/404 |
| 4,936,316 | A | * | 6/1990  | Jewett ............................ 600/588 |
| 5,040,536 | A |   | 8/1991  | Riff |
| 5,050,612 | A |   | 9/1991  | Matsumura |

(Continued)

FOREIGN PATENT DOCUMENTS

| DE | 198 31 109 | 1/2000 |
| DE | 100 24 103 | 11/2001 |

(Continued)

OTHER PUBLICATIONS

Final Office Action dated Oct. 26, 2011 for U.S. Appl. No. 12/856,255, (8 pgs.).

(Continued)

*Primary Examiner* — Max Hindenburg
*Assistant Examiner* — Renee Danega
(74) *Attorney, Agent, or Firm* — Shumaker & Sieffert, P.A.

(57) ABSTRACT

A wearable ambulatory data recorder that senses physiological parameters of a patient, and stores physiological parameter data for later retrieval, as well as techniques for using such a wearable ambulatory data recorder, are described. The data recorder includes one or more sensors located on or within a housing. The data recorder may include an adhesive layer for attachment to a patient. In some embodiments, the housing may be within a patch, e.g., bandage, which includes the adhesive layer. The housing may be waterproof. Features of the data recorder such as size, waterproofness, and inclusion of an adhesive may allow the data recorder to be unobtrusively worn by a patient during a variety of daily activities. The data recorder may be for single use and thereafter disposable.

14 Claims, 17 Drawing Sheets

U.S. PATENT DOCUMENTS

| | | | |
|---|---|---|---|
| 5,058,584 A | 10/1991 | Bourgeois | |
| 5,125,412 A | 6/1992 | Thornton | |
| 5,154,180 A | 10/1992 | Blanchet et al. | |
| 5,233,984 A | 8/1993 | Thompson | |
| 5,275,159 A | 1/1994 | Griebel | |
| 5,335,657 A | 8/1994 | Terry, Jr. et al. | |
| 5,337,758 A | 8/1994 | Moore et al. | |
| 5,342,409 A | 8/1994 | Mullett | |
| 5,469,861 A | 11/1995 | Piscopo et al. | |
| 5,476,483 A | 12/1995 | Bornzin et al. | |
| 5,514,162 A | 5/1996 | Bornzin et al. | |
| 5,593,431 A | 1/1997 | Sheldon | |
| 5,622,428 A | 4/1997 | Bonnet | |
| 5,645,053 A | 7/1997 | Remmers et al. | |
| 5,732,696 A | 3/1998 | Rapoport et al. | |
| 5,782,884 A | 7/1998 | Stotts et al. | |
| 5,851,193 A | 12/1998 | Arikka et al. | |
| 5,895,371 A | 4/1999 | Levitas et al. | |
| 5,904,708 A | 5/1999 | Goedeke | |
| 5,919,149 A | 7/1999 | Allum | |
| 5,941,906 A | 8/1999 | Barreras, Sr. et al. | |
| 5,944,680 A | 8/1999 | Christopherson et al. | |
| 6,044,297 A | 3/2000 | Sheldon et al. | |
| 6,045,513 A | 4/2000 | Stone et al. | |
| 6,059,576 A | 5/2000 | Brann | |
| 6,095,991 A | 8/2000 | Krausman et al. | |
| 6,102,874 A | 8/2000 | Stone et al. | |
| 6,120,467 A | 9/2000 | Schallhorn | |
| 6,128,534 A | 10/2000 | Park et al. | |
| 6,157,857 A | 12/2000 | Dimpfel | |
| 6,165,143 A | 12/2000 | van Lummel | |
| 6,200,265 B1 | 3/2001 | Walsh et al. | |
| 6,259,948 B1 | 7/2001 | Florio et al. | |
| 6,280,409 B1 | 8/2001 | Stone et al. | |
| 6,296,606 B1 | 10/2001 | Goldberg et al. | |
| 6,308,098 B1 | 10/2001 | Meyer | |
| 6,315,740 B1 | 11/2001 | Singh | |
| 6,351,672 B1 | 2/2002 | Park et al. | |
| 6,416,471 B1 | 7/2002 | Kumar et al. | |
| 6,440,090 B1 | 8/2002 | Schallhorn | |
| 6,449,508 B1 | 9/2002 | Sheldon et al. | |
| 6,459,934 B1 | 10/2002 | Kadhiresan | |
| 6,466,821 B1 | 10/2002 | Pianca et al. | |
| 6,468,234 B1 | 10/2002 | Van der Loos et al. | |
| 6,514,218 B2 | 2/2003 | Yamamoto | |
| 6,539,249 B1 | 3/2003 | Kadhiresan et al. | |
| 6,574,507 B1 | 6/2003 | Bonnet | |
| 6,605,038 B1 | 8/2003 | Teller et al. | |
| 6,611,783 B2 * | 8/2003 | Kelly et al. | 702/150 |
| 6,641,542 B2 | 11/2003 | Cho et al. | |
| 6,659,968 B1 | 12/2003 | McClure | |
| 6,687,538 B1 | 2/2004 | Hrdlicka et al. | |
| 6,731,984 B2 | 5/2004 | Cho et al. | |
| 6,752,766 B2 | 6/2004 | Kowallik et al. | |
| 6,773,404 B2 | 8/2004 | Poezevera et al. | |
| 6,878,121 B2 | 4/2005 | Krausman et al. | |
| 6,884,596 B2 | 4/2005 | Civelli et al. | |
| 6,890,306 B2 | 5/2005 | Poezevera | |
| 6,928,324 B2 | 8/2005 | Park et al. | |
| 6,964,641 B2 | 11/2005 | Cho et al. | |
| 6,997,882 B1 | 2/2006 | Parker et al. | |
| 7,117,036 B2 | 10/2006 | Florio | |
| 7,141,034 B2 | 11/2006 | Eppstein et al. | |
| 7,162,304 B1 | 1/2007 | Bradley | |
| 7,383,728 B2 * | 6/2008 | Noble et al. | 73/379.01 |
| 8,016,776 B2 | 9/2011 | Bourget et al. | |
| 2001/0037067 A1 | 11/2001 | Tchou et al. | |
| 2002/0077562 A1 | 6/2002 | Kalgren et al. | |
| 2002/0091308 A1 | 7/2002 | Kipshidze et al. | |
| 2002/0161412 A1 | 10/2002 | Sun et al. | |
| 2002/0169485 A1 | 11/2002 | Pless et al. | |
| 2002/0193697 A1 | 12/2002 | Cho et al. | |
| 2002/0193839 A1 | 12/2002 | Cho et al. | |
| 2003/0004423 A1 | 1/2003 | Lavie et al. | |
| 2003/0139692 A1 | 7/2003 | Barrey et al. | |
| 2003/0149457 A1 | 8/2003 | Tcheng et al. | |
| 2003/0153953 A1 | 8/2003 | Park et al. | |
| 2003/0153955 A1 | 8/2003 | Park et al. | |
| 2003/0153956 A1 | 8/2003 | Park et al. | |
| 2003/0163059 A1 | 8/2003 | Poezevera et al. | |
| 2003/0171791 A1 | 9/2003 | KenKnight et al. | |
| 2003/0212445 A1 | 11/2003 | Weinberg | |
| 2004/0002741 A1 | 1/2004 | Weinberg | |
| 2004/0002742 A1 | 1/2004 | Florio | |
| 2004/0015103 A1 | 1/2004 | Aminian et al. | |
| 2004/0049132 A1 | 3/2004 | Barron et al. | |
| 2004/0102814 A1 | 5/2004 | Sorensen et al. | |
| 2004/0111040 A1 | 6/2004 | Ni et al. | |
| 2004/0111041 A1 | 6/2004 | Ni et al. | |
| 2005/0042589 A1 | 2/2005 | Hatlestad et al. | |
| 2005/0113710 A1 | 5/2005 | Stahmann et al. | |
| 2005/0177192 A1 | 8/2005 | Rezai et al. | |
| 2005/0209511 A1 | 9/2005 | Heruth et al. | |
| 2005/0209512 A1 | 9/2005 | Heruth et al. | |
| 2005/0209513 A1 | 9/2005 | Heruth et al. | |
| 2005/0209643 A1 | 9/2005 | Heruth et al. | |
| 2005/0209644 A1 | 9/2005 | Heruth et al. | |
| 2005/0209645 A1 | 9/2005 | Heruth et al. | |
| 2005/0215847 A1 | 9/2005 | Heruth et al. | |
| 2005/0215947 A1 | 9/2005 | Heruth et al. | |
| 2005/0216064 A1 | 9/2005 | Heruth et al. | |
| 2005/0222522 A1 | 10/2005 | Heruth et al. | |
| 2005/0222643 A1 | 10/2005 | Heruth et al. | |
| 2005/0234514 A1 | 10/2005 | Heruth et al. | |
| 2005/0234518 A1 | 10/2005 | Heruth et al. | |
| 2005/0240086 A1 | 10/2005 | Akay | |
| 2005/0240242 A1 | 10/2005 | DiLorenzo | |
| 2005/0245988 A1 | 11/2005 | Miesel | |
| 2006/0282175 A1 * | 12/2006 | Haines et al. | 623/24 |
| 2007/0046408 A1 | 3/2007 | Shim | |
| 2007/0129622 A1 | 6/2007 | Bourget et al. | |
| 2007/0129769 A1 | 6/2007 | Bourget et al. | |

FOREIGN PATENT DOCUMENTS

| | | |
|---|---|---|
| EP | 0 564 803 A1 | 10/1993 |
| EP | 0 849 715 B1 | 6/1998 |
| EP | 1 195 139 A1 | 4/2002 |
| EP | 1 291 036 A2 | 3/2003 |
| EP | 1 308 182 A2 | 5/2003 |
| EP | 1 437 159 A1 | 7/2004 |
| GB | 2 330 912 A | 5/1999 |
| WO | WO 98/00197 | 1/1998 |
| WO | WO 99/13765 | 3/1999 |
| WO | WO 01/37930 | 5/2001 |
| WO | WO 02/28282 | 4/2002 |
| WO | WO 02/41771 | 5/2002 |
| WO | WO 02/087433 | 11/2002 |
| WO | WO 02/096512 | 12/2002 |
| WO | WO 02/100267 | 12/2002 |
| WO | WO 03/024325 | 3/2003 |
| WO | WO 03/051356 | 6/2003 |
| WO | WO 03/065891 | 8/2003 |
| WO | WO 2005/028029 | 3/2005 |
| WO | WO 2005/035050 | 4/2005 |

OTHER PUBLICATIONS

Request for Continued Examination and Responsive Amendment dated Dec. 15, 2011 for U.S. Appl. No. 12/856,255, (11 pgs.).

Office Action dated Mar. 27, 2012 for U.S. Appl. No. 13/362,785, (10 pgs.).

Responsive Amendment dated Jun. 27, 2012 for U.S. Appl. No. 13/362,785, (13 pgs.).

Office Action dated Jul. 26, 2012 for U.S. Appl. No. 13/362,785, (5 pgs.).

Amzica, "Physiology of Sleep and Wakefulness as it Relates to the Physiology of Epilepsy," Journal of Clinical Neurophysiology, American Clinical Neurophysiology Society, 19(6), pp. 488-503, (2002).

Dinner, "Effect of Sleep on Epilepsy," Journal of Clinical Neurophysiology, American Clinical Neurophysiology Society, 19(6), pp. 504-513, (2002).

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, (2002).

Mendez et al. "Interactions Between Sleep and Epilepsy," Journal of Clinical Neurophysiology, American Clinical Neurophysiology Society, 18(2), pp. 106-127, (2001).

"MiniMitter® Physiological and Behavioral Monitoring for Humans and Animals," http://www.minimitter.com/Products/Actiwatch, 3 pgs. Feb. 20, 2006.

"IBM & Citzen Watch develop Linux-based 'WatchPad'," 5 pgs., http://www.linuxdevices.com/news/NS6580187845.html, Feb. 20, 2006.

"Design Competition: Runners-Up for the Best Three Designs," EPN, vol. 26, No. 1, 1 pg., (2002).

"Watch," Wikipedia, the free encyclopedia, 6 pgs., http://en.wikipedia.org/wiki/Watch, Feb. 20, 2006.

Kassam, "2005 EDP Topic 'MK4': Tremor Data-Logger for Parkinson's Disease Patients," http://www.ee.ryerson.ca/~courses/edp2005/MK4.html, 3 pgs., Feb. 20, 2006.

Tuisku, "Motor Activity Measured by Actometry in Neuropsychiatric Disorders," Department of Psychiatry, University of Helsinski, Helsinki, Finland, 115 pgs. (2002).

Smith et al., "Presleep Cognitions in Patients with Insomnia Secondary to Chronic Pain," Journal of Behavioral Medicine, vol. 24, No. 1, pp. 93-114, (2001).

Smith et al. "How do sleep disturbance and chronic pain inter-relate? Insights from the longitudinal and cognitive-behavioral clinical trials literature," Sleep Medicine Reviews, YSMRV 286, pp. 1-14, (2003).

Goodrich et al., "The Prediction of Pain Using Measures of Sleep Quality," Pain Digest, 8:23-25, (1998).

"Analysis of heart rate dynamics by methods derived from nonlinear mathematics: Clinical applicability and prognostic significance" http:herkules.oulu.fi.isbn9514250133/html, 4 pgs., (2004).

Kerr et al., "Analysis of the sit-stand-sit movement cycle in normal subjects," Clinical Biomechanics, vol. 12, No. 4, pp. 236-245, (1997).

Aminian et al. "Physical Activity Monitoring Based on Accelerometry: Validation and Comparison with Video Observation," Medical & Biological Engineering & Computing, vol. 37, No. 2, pp. 304-308 (1999).

Medcare—A Global Leader in Sleep Diagnostics, Embletta Recording System, http://www.medcare.com/products/diagnostic/embletta/, 2 pgs. Jan. 31, 2005.

Medcare—A Global Leader in Sleep Diagnostics, Somnologica for Embletta, http://www.medcare.com/products/diagnostic/embletta/SomnoEmbletta/index.asp, 1 pg. Jan. 31, 2005.

MAP Medizin-Technologie GmbH, Poly-MESAM®, http://195.244.124.130/map/de/eng/map_med.nsf/smsall/70564A3FCBE4188AC1256EF4.., 4 pgs. Jan. 31, 2005.

Merlin, http://www.aha.ru/~pir/english/merlin/, 4 pgs. Jan. 31, 2005.

Sleep Solutions—PR Newswire: Sleep Solutions Introduces NovaSom™ QSG™ for PSG.., http://www.sleep-solutions.com/press_room/novasom.htm, 2 pgs. Jan. 31, 2005.

Itamar Medical Information, http://itamar-medical.com/content.asp?id-id=31, 2 pgs. Jan. 31, 2005.

Criticare System Inc.,-504DX Portable Pulse Oximeter, http://www.csiusa.com/504dx.html, 4 pgs. Jan. 31, 2005.

Snap® Laboratories, Product Fact Sheet, http://www.snaplab.com/mp_fact.htm, 2 pgs. Jan. 31, 2005.

Sleep Strip & Bite Strip, http://ww.quietsleep.com/snoringapnea/sleepstrip.htm, 8 pgs. Jan. 31, 2005.

"Bitestrip Flier," downloaded from Internet Archive of www.quietsleep.com dated Jan. 29, 2005 http://web.archive.org/web/20041124080003/www.quietsleep.com/pdf/Bitestrip+Flier.pdf.

"Bilateral Comparisons of the BiteStrip Bruxism Device and Masseter EMG Bruxism Events" downloaded from Internet Archive of www.quietsleep.com dated Jan. 29, 2005 http://web.archive.org/web/20041124075114/www.quietsleep.com/pdf/Bilateral+Comparisons.pdf.

"The BiteStrip: A Novel Screener for Sleep Bruxism," downloaded from Internet Archive of www.quietsleep.com dated Jan. 29, 2005 http://web.archive.org/web/20041124072922/www.quietsleep.com/pdf/BiteStrip-+Novel+Screener.pdf.

Office Action dated Sep. 18, 2008 for U.S. Appl. No. 11/413,619 (9 pgs.).

Responsive Amendment dated Dec. 17, 2008 for U.S. Appl. No. 11/413,619 (11 pgs.).

Notification of Transmittal of the International Search Report and the Written Opinion of the International Searching Authority, or the Declaration, dated Apr. 20, 2007 for corresponding International Application No. PCT/US2006/045554, filed Nov. 29, 2006, (12 pgs.).

Notification of Transmittal of the International Preliminary Report on Patentability dated Jun. 12, 2008 for corresponding PCT Application No. PCT/US2006/045554 (7 pgs.).

Office Action dated May 8, 2009 for U.S. Appl. No. 11/691,391 (8 pgs.).

Responsive Amendment dated Aug. 5, 2009 for U.S. Appl. No. 11/691,391 (11 pgs.).

Office Action dated Feb. 2, 2010 for U.S. Appl. No. 12/351,414 (11 pgs.).

Office Action dated Feb. 19, 2010 for U.S. Appl. No. 11/413,619 (10 pgs.).

Office Action dated Mar. 12, 2010 for U.S. Appl. No. 11/691,413 (7 pgs.).

Pre-Appeal Brief Request for Review dated May 19, 2010 for U.S. Appl. No. 11/413,619 (5 pgs.).

Office Action dated Mar. 9, 2009 for U.S. Appl. No. 11/414,507 (11 pgs.).

Responsive Amendment dated Jun. 9, 2009 for U.S. Appl. No. 11/414,507 (11 pgs.).

Final Office Action dated Oct. 19, 2009 for U.S. Appl. No. 11/414,507 (11 pgs.).

Request for Continued Examination and Responsive Amendment dated Dec. 18, 2009 for U.S. Appl. No. 11/414,507 (16 pgs.).

* cited by examiner

| PARAMETER SET | PARAMETERS | SLEEP EFFICIENCY | SLEEP LATENCY | DEEP SLEEP |
|---|---|---|---|---|
| 1 | PA = 5.5V<br>PW = 210ms<br>PR = 90Hz | 85% | 20 min. | 4 hours |
| 2 | PA = 5V<br>PW = 190ms<br>PR = 95Hz | 75% | 25 min. | 3.8 hours |
| ••• | | | | |
| N | PA = 4.6V<br>PW = 215ms<br>PR = 80Hz | 70% | 38 min. | 3.0 hours |

| PARAMETER SET | PARAMETERS | % OF TIME ACTIVE | COUNTS/HOUR |
|---|---|---|---|
| 1 | PA = 5.5V<br>PW = 210ms<br>PR = 90Hz | 75%<br>(15% HIGH) | 100 |
| 2 | PA = 5V<br>PW = 190ms<br>PR = 95Hz | 60%<br>(5% HIGH) | 67 |
| ••• | | | |
| N | PA = 4.6V<br>PW = 215ms<br>PR = 80Hz | 55%<br>(8% HIGH) | 72 |

| PARAMETER SET | PARAMETERS | % UPRIGHT | TRANSITIONS/HOUR |
|---|---|---|---|
| 1 | PA = 5.5V<br>PW = 210ms<br>PR = 90Hz | 75% | 15 |
| 2 | PA = 5V<br>PW = 190ms<br>PR = 95Hz | 60% | 9 |
| ••• | | | |
| N | PA = 4.6V<br>PW = 215ms<br>PR = 80Hz | 55% | 8 |

FIG. 15

WEARABLE AMBULATORY DATA RECORDER

This application is a continuation of U.S. application Ser. No. 11/413,619, filed Apr. 28, 2006, which claims the benefit of U.S. provisional application No. 60/742,002, filed Dec. 2, 2005, and U.S. provisional application No. 60/785,657, filed Mar. 24, 2006. The entire content of each of these three applications is incorporated by reference herein.

TECHNICAL FIELD

The invention relates to medical devices and, more particularly, to medical devices that monitor physiological parameters.

BACKGROUND

The quality of a patient's life may be an indication of the severity or progression of a symptom or aliment, and also of the efficacy of a therapy to treat the symptom or ailment. For example, quality of life is directly related to the level of pain a patient experiences in everyday life. Accordingly, the quality of the patient's life may indicate the severity of the pain and effectiveness of therapies to treat the pain. The quality of a patient's life may similarly be impacted by: movement disorders, such as tremor, Parkinson's disease, spasticity, and multiple sclerosis; psychological disorders, such as depression, mania, bipolar disorder, or obsessive-compulsive disorder; cardiac disorders, such as congestive heart failure or arrhythmia; gastric disorders, such as gastroparesis; or obesity.

The quality of sleep experienced by a patient, the overall activity level of a patient, or the amount of time a patient spends engaged in particular activities, in particular postures, or above particular activity levels may indicate the quality of the patient's life, and thereby the effectiveness of a therapy used to treat a symptom or disorder, such as those identified above. However, such life quality metrics are not typically quantified for evaluation of disease state or therapy. For example, a major limitation of most of the pain literature is the poor assessment of sleep conducted in many studies. There are relatively few objective polysomnographic and actigraphic assessments, and most studies rely solely on retrospective subjective self-report measures of sleep disturbance.

Chronic pain may cause a patient to avoid particular activities, or activity in general, where such activities increase the pain experienced by the patient. When a patient is inactive, he or she may be more likely to be recumbent, i.e., lying down, or sitting, and may change postures less frequently. Additionally, sleep disturbance is perhaps one of the most prevalent complaints of patients with chronically painful conditions. Quality of sleep, quantity of sleep, and trouble falling asleep may be related to the intensity and frequency of pain.

Similarly, the difficulty walking or otherwise moving experienced by patients with movement disorders may cause such patients to avoid particular activities or posture, or movement in general, to the extent possible. Further, the uncontrolled movements associated with such movement disorders may cause a patient to have difficulty falling asleep, disturb the patient's sleep, or cause the patient to have difficulty achieving deeper sleep states. Additionally, many psychological disorders disturb a patient's sleep, and cause them to engage in less activity during the day. Patients with depression often spend much of the day in bed or otherwise recumbent.

Further, in some cases, poor sleep quality may increase the symptoms experienced by a patient due to an ailment. For example, poor sleep quality has been linked to increased pain symptoms in chronic pain patients, due to lowering the pain threshold of the patient. Poor sleep may similarly increase tremor in movement disorder patients or the level of symptoms for some psychological disorders. The link between poor sleep quality and increased symptoms is not limited to ailments that negatively impact sleep quality, such as those listed above. Nonetheless, the condition of a patient with such an ailment may progressively worsen when symptoms disturb sleep quality, which in turn increases the frequency and/or intensity of symptoms. The increased symptoms may, in turn, limit patient activity during the day, and further disturb sleep quality.

SUMMARY

In general, the invention is directed to a wearable ambulatory data recorder that senses physiological parameters of a patient, and stores physiological parameter data based on the sensed parameters for later retrieval, as well as techniques for using such a wearable ambulatory data recorder. The data recorder includes one or more sensors located on or within a housing, where a sensor may detect a physiological parameter such as heart activity, brain activity, temperature, tissue oxygenation, activity, or posture. Data may be recorded for a time period of a few minutes to multiple days to provide objective data regarding the quality of life of a patient, e.g., the quality of sleep, or degree of activity or postural changes, of the patient. Such data may be used, as examples, for patient monitoring or diagnosis, to provide closed-loop feedback for a therapy, or to evaluate the effectiveness of a therapy delivered to the patient. The data may be transferred to a computer for post-processing and review.

The size of the data recorder may allow it to be worn in an unobtrusive manner that does not interfere with patient activities. As examples, the thickness of the housing of the data recorder may be approximately 0.6 centimeters. Further, in some embodiments, a volume of the housing may be approximately 6.3 cubic centimeters. The data recorder may include an adhesive layer for attachment to a patient. In some embodiments, the housing may be within a patch, which may be bandage-like, that includes the adhesive layer. The housing may be waterproof to allow the patient to continue normal daily activities that include physical activity, swimming, or showing. Additional features of the data recorder may include inexpensive manufacturing which may allow the data recorder to be disposable after patient use.

Data stored by the data recorder may be used to diagnose patient conditions, to provide closed-loop feedback for therapies, or to monitor patient response to received therapies. For example, the data recorder may be used to gather data before, during, or after stimulation or drug therapy to monitor any changes in patient activity or physiological parameters. In some embodiments, the data recorder, a medical device, or a separate computing device associates physiological parameter data gathered by the data recorder with a plurality of therapy parameter sets used by the medical device to control delivery to a patient over time.

In this manner, a user may compare the relative efficacy of the therapy parameter sets by comparing the physiological parameter data associated with the therapy parameter sets. The data recorder may record data during delivery of therapy by an implantable medical device according to a plurality of parameter sets during normal use, e.g., as the patient selects and modifies parameter sets. As another example, the data recorder may record physiological parameter data during a "trialing" phase of a therapy, such as neurostimulation for treatment of pain or movement disorders, during which a plurality of therapy parameter sets are trialed over a relatively short period of time. During the trialing phase, therapy may be delivered by an implantable medical device, or an external trial device, in which cast the physiological parameter data may be used to assist in the identification of efficacious parameter sets for eventual programming of the implanted medical device.

In some embodiments, the data recorder, medical device, or other computing device may further process the physiological parameter data to determine values for one or more metrics indicative of the quality of a patient's life. As examples, sleep quality, activity, or posture metrics may be determined. Metrics indicative of sleep quality may include sleep efficiency, sleep latency, and time spent in deeper sleep states, e.g., one or both of the S3 and S4 sleep state. Activity metrics may include percentages or lengths of time above a threshold activity level, while posture metrics may include numbers of posture transitions, or length or percentage of time spent in particular postures, e.g., upright. Such metric values may be determined for each of a plurality of therapy parameter sets based on the physiological parameter data associated with the parameter sets, and presented to a user to allow evaluation, comparison, and selection of therapy parameter sets.

In embodiments in which the wearable ambulatory data recorder includes a posture sensor, e.g., a multi-axis accelerometer, the invention provides techniques for calibrating the sensor. In particular, it may be desirable to calibrate the sensor by having the patient assume a predetermined posture, e.g., upright, and then signaling the recorder that the patient is in the predetermined posture. Accordingly, the data recorder identifies a current posture of the patient in response to the signal, and associates that posture with the predetermined posture to calibrate the sensor.

The data recorder may include a removable element, e.g., attached to the housing of the data recorder, and may detect removal of the element as the signal to calibrate the sensor, e.g., as the signal that the patient is in the predetermined posture. In some embodiments, removal of the element also powers on the data recorder, which calibrates the sensor in response to being powered-on. The element may be, as an example, a magnet, which may be attached to the data recorder by an adhesive. In some embodiments, the magnet is included in a backing layer for an adhesive that the attaches the data recorder to the patient, or a different backing layer, attached by a different adhesive, that is removed after attachment of the data recorder to the patient.

In one embodiment, the disclosure provides an external wearable ambulatory data recorder comprising a housing, a sensor that generates a signal as a function of posture of a patient that wears the data recorder within the housing, a memory within the housing, a processor within the housing that receives signal from the sensor, and stores posture data within the memory for the patient based on the signal, and an element removably attached to the data recorder. The processor calibrates the sensor in response to removal of the element.

In another embodiment, the disclosure provides an external wearable ambulatory data recorder comprising a housing, means within the housing for sensing posture of a patient that wears the data recorder and generating posture data, means within the housing for storing the posture data, an element removably attached to the housing, and means for calibrating the posture sensing means in response to removal of the element.

In another embodiment, the disclosure provides a method comprising sensing posture of a patient via an external ambulatory data recorder worn by the patient, storing posture data within a memory of the data recorder, detecting removal of an element from the data recorder, and calibrating posture sensing in response to the removal.

In another embodiment, the disclosure provides a method comprising delivering a therapy to a patient via a medical device, sensing a plurality of physiological parameters of the patient via an external wearable ambulatory data recorder during delivery of the therapy, the data recorder separate from the medical device, and providing the physiological parameter data to a user for evaluation of the therapy, the physiological parameter data determined based on the sensed physiological parameters.

In another embodiment, the disclosure provides a system comprising a medical device that delivers a therapy to a patient a separate external wearable ambulatory data recorder that senses a plurality of physiological parameters of the patient during delivery of the therapy, and stores physiological parameter data based on the sensed physiological parameters, and a processor that provides the physiological parameter data to a user for evaluation of the therapy.

In another embodiment, the disclosure provides a system comprising means for delivering a therapy to a patient, separately housing external means for sensing a plurality of physiological parameters of the patient during delivery of the therapy means for determining physiological parameter data based on the sensed physiological parameters, and means for providing the physiological parameter data to a user for evaluation of the therapy.

In other embodiments, the invention is directed to computer-readable media containing instructions that cause a programmable processor to perform any one or more of the methods and techniques described herein.

Embodiments of the invention may provide one or more advantages. For example, a data recorder according to the invention may provide a physician with objective data related to patient activity and patient quality of life, rather than subjective recollections from the patient. The data recorder may also eliminate bulky or tethered data recording systems that limit patient activity and contribute to patient awareness of monitoring. In addition, a small, wearable, and waterproof data recorder may provide a simple disposable solution to patient monitoring that may be beneficial to a wide variety of health care applications. In some embodiments, calibration of a posture sensor of the data recorder may be relatively easy in that it may involve removing a single item from the recorder.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 13-15 are conceptual diagrams illustrating presentation of various example quality of life metric values associated with therapy parameter sets to a user.

DETAILED DESCRIPTION

Figure 1:
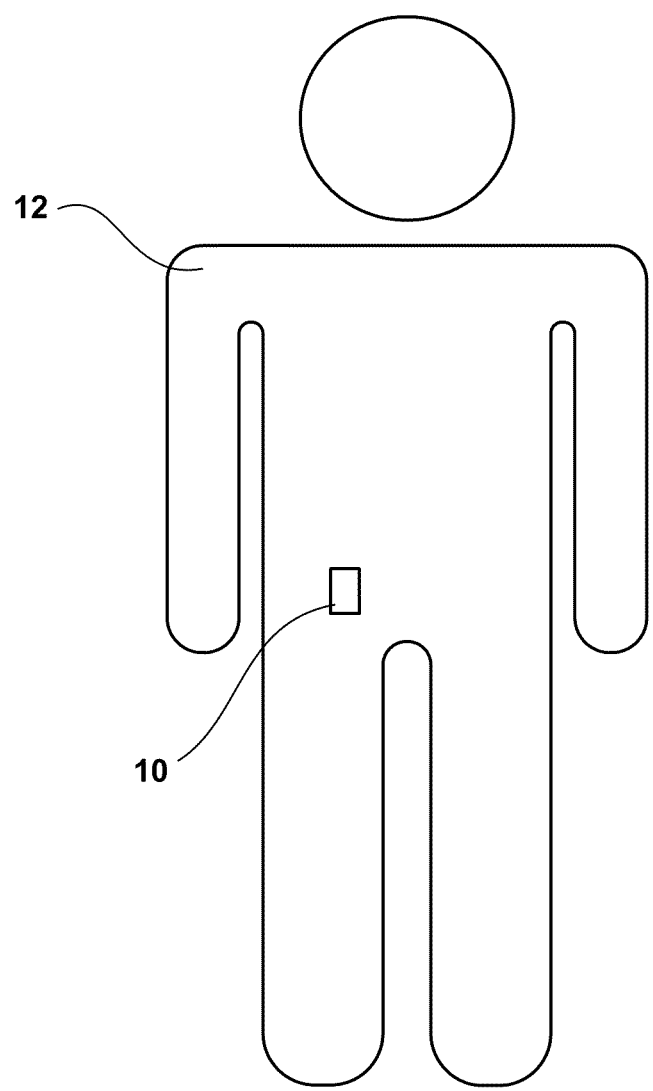
FIG. 1 is a conceptual diagram illustrating an example wearable ambulatory data recorder (ADR) attached to a patient at an example location.

FIG. 1 is a conceptual diagram illustrating an example wearable ambulatory data recorder (ADR) 10 attached to a patient 12 at an example location. ADR 10 includes at least one sensor that senses a physiological parameter of a patient, and may include a variety of sensors (not shown in FIG. 1) to sense a variety of physiological parameters of the patient, as will be described in greater detail below. ADR 10 may store physiological parameter data determined based on the sensed physiological parameters for later retrieval and presentation to a user. In this manner, ADR 10 may facilitate collection of physiological parameter data for patient monitoring, patient diagnosis, or therapy evaluation.

In the illustrated embodiment, ADR 10 is attached to the abdomen of patient 12. However, ADR 10 may be attached to patient 12 at any location, including the chest, back, pelvis, or head of the patient. In some embodiments, ADR 10 may be attached to patient 12 at a location proximate to an implantable medical device. In other embodiments, ADR may be implanted proximate to an intended location for an implantable medical device, in order to approximate the sensing that may be later performed by the implantable medical device.

ADR 10 may be attached to patient 12 by an adhesive. In other embodiments, the ADR may be attached to patient by a band, belt, or sutures. The invention is not limited to any particular attachment mechanism, although an adhesive may allow ADR 10 to be attached to patient 12 more comfortably and unobtrusively than other attachment mechanisms Further, the sensors may be located on or within a housing of the ADR, which may allow ADR 10 to sense physiological parameters without leads. Additionally, ADR 10 may be waterproof and small relative to existing data recorders with similar functional capabilities. The waterproofness, size, lack of leads, and adhesive attachment of ADR 10 may contribute to the comfort and unobtrusiveness of ADR 10, allowing patient 12 to wear ADR substantially continuously over an extended period of time and during a variety of daily activities.

Figure 2:
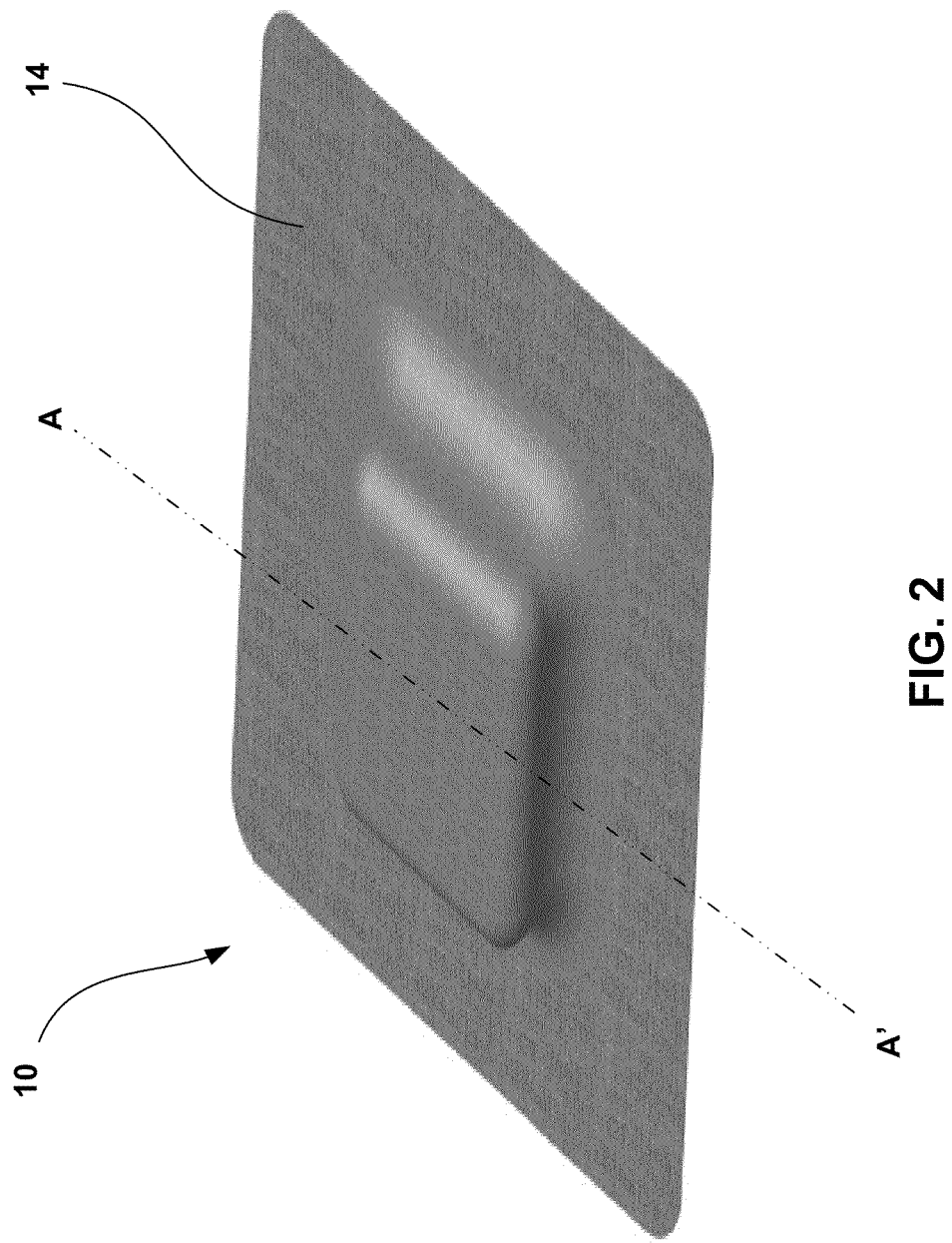
FIG. 2 is perspective view of the wearable ADR of FIG. 1.

FIG. 2 is perspective view of wearable ADR. In the illustrated embodiment, ADR 10 includes a patch 14, which may be a bandage or bandage-like, for attachment to patient 12. Patch 14 may include an adhesive layer (not shown in FIG. 2) for attachment of ADR 10 to patient. Patch 14 may be made of any of a variety of conformable, flexible materials with relatively low durometers. Patch 14 may be made from any materials known for use in bandages. As examples, bandage 14 may be made from polymers, elastomers, foams, hydrogels, polytetraflouroethylene (PTFE), expanded PTFE, silicone, silicone gel, or the like. Including such materials in patch 14 may improve the comfort and unobtrusiveness of ADR 10 when worn by patient 12.

Figure 3A:
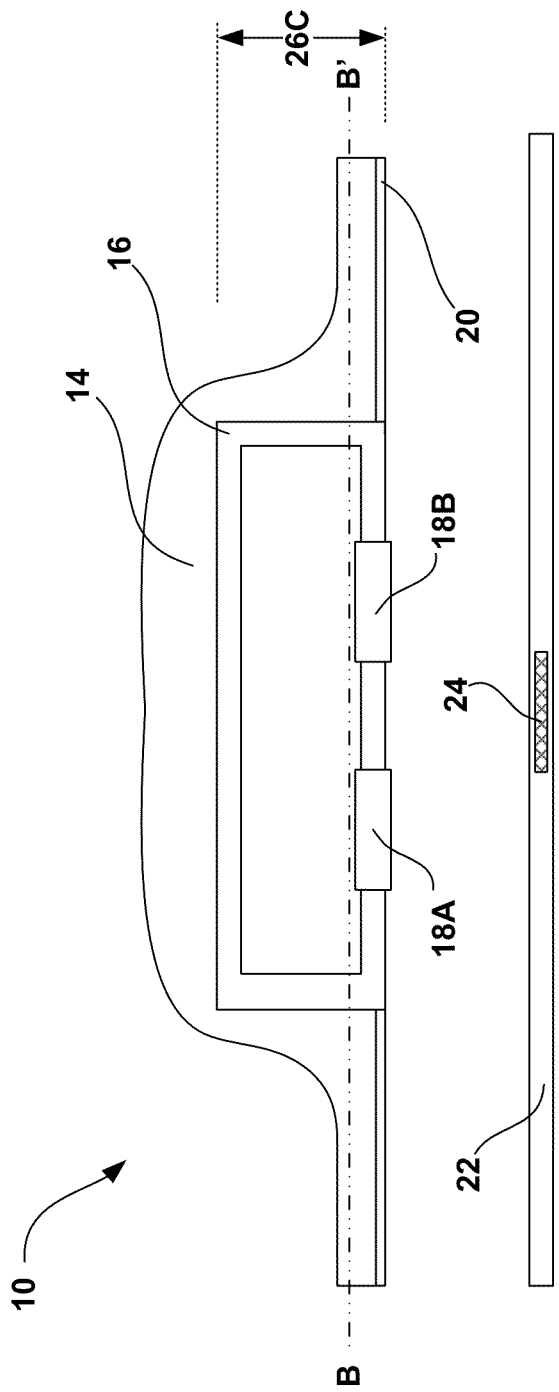
FIG. 3A is a cross-sectional side-view further illustrating the wearable ADR of FIG. 1, the cross section taken along line A-A' of FIG. 2.

FIG. 3A is a cross-sectional side-view further illustrating wearable ADR 10, the cross section taken along line A-A' of FIG. 2. As illustrated in FIG. 3A, ADR 10 includes a housing 16 within patch 14. Housing 16 may be made of relatively rigid materials, and may be waterproof. Example materials for housing 16 may include plastics, polymers, metals, polyvinylchloride, or the like.

In the illustrated example, the sensors of ADR 10 include two electrodes 18A and 18B (collectively "electrodes 18") formed on or within housing 16. ADR 10 may include any number of electrodes 18. ADR 10 may additionally or alternatively include other sensors on or within housing 16, such as accelerometers or optical sensors. Sensors may be formed on housing 16 to, for example, facilitate contact of the sensor with tissue, e.g., skin, of the patient.

An adhesive layer 20 for attaching ADR 10 to patient 12 is also illustrated in FIG. 3A. Adhesive layer 20 may include any of a variety of contact adhesives known to be usable for bandages or other applications in which an object is adhesively attached to the skin of a patient. A removable backing layer 22 may be attached to adhesive 20 prior to application of ADR 10 to patient 12, e.g., during shipment and other handling of the ADR, and removed for attachment of ADR 10 to patient.

In some embodiments, ADR 10 may be shipped and handled in a no or low-power shipment mode to reduce consumption of an internal power source, e.g., battery, of the ADR prior to use. ADR 10 may detect removal of backing layer 22 as an indication that the ADR is about to be attached to the patient for sensing physiological parameters of the patient. In response to detecting removal of the backing layer, ADR 10 may enter a powered or fully-functional mode to allow sensing of physiological parameters.

For example, as illustrated in FIG. 3A, backing layer 22 may include a magnet 24. ADR 10 may detect removal of the backing layer by detecting removal of the magnet from a proximate position to ADR 10. As an example, removal of the backing layer, and thus the magnet, may actuate a switch within ADR 10 to couple an internal power source of the ADR to other components of the ADR, e.g., to power on the ADR.

However, the invention is not limited to embodiments in which a removable element is a backing layer or magnet. For example, in some embodiments, an ADR may be coupled to a removable circuit component. In such embodiments, the ADR may detect an open-circuit or impedance change resulting from removal of the component.

In embodiments in which ADR 10 includes a posture sensor, e.g., a multi-axis accelerometer, removal of backing layer 22 and magnet 24, or some other removable element, may also cause ADR 10 to calibrate the sensor. One example technique for calibrating the sensor involves having the patient assume a predetermined posture, e.g., upright, so that ADR 10 may associate a current sensed posture with the predetermined posture. ADR 10 may calibrate the posture sensor immediately after removal of backing layer 22 and magnet 24, which in some embodiment is immediately after a power on or power up, or may wait a predetermined time after removal to allow ADR 10 to be attached to patient 12, and patient 12 to assume the predetermined posture.

FIG. 3A also illustrates a thickness 26C of housing 16. A smaller thickness 26C may allow greater comfort and unobtrusiveness of ADR 10 when worn by patient 12. Thickness 26C may be less than approximately 1.5 centimeters, less than approximately 1 centimeter, or approximately 0.6 centimeters. These example thicknesses 26C of housing 16 may improve the comfort and unobtrusiveness of ADR 10 when worn by patient 12.

Figure 3B:
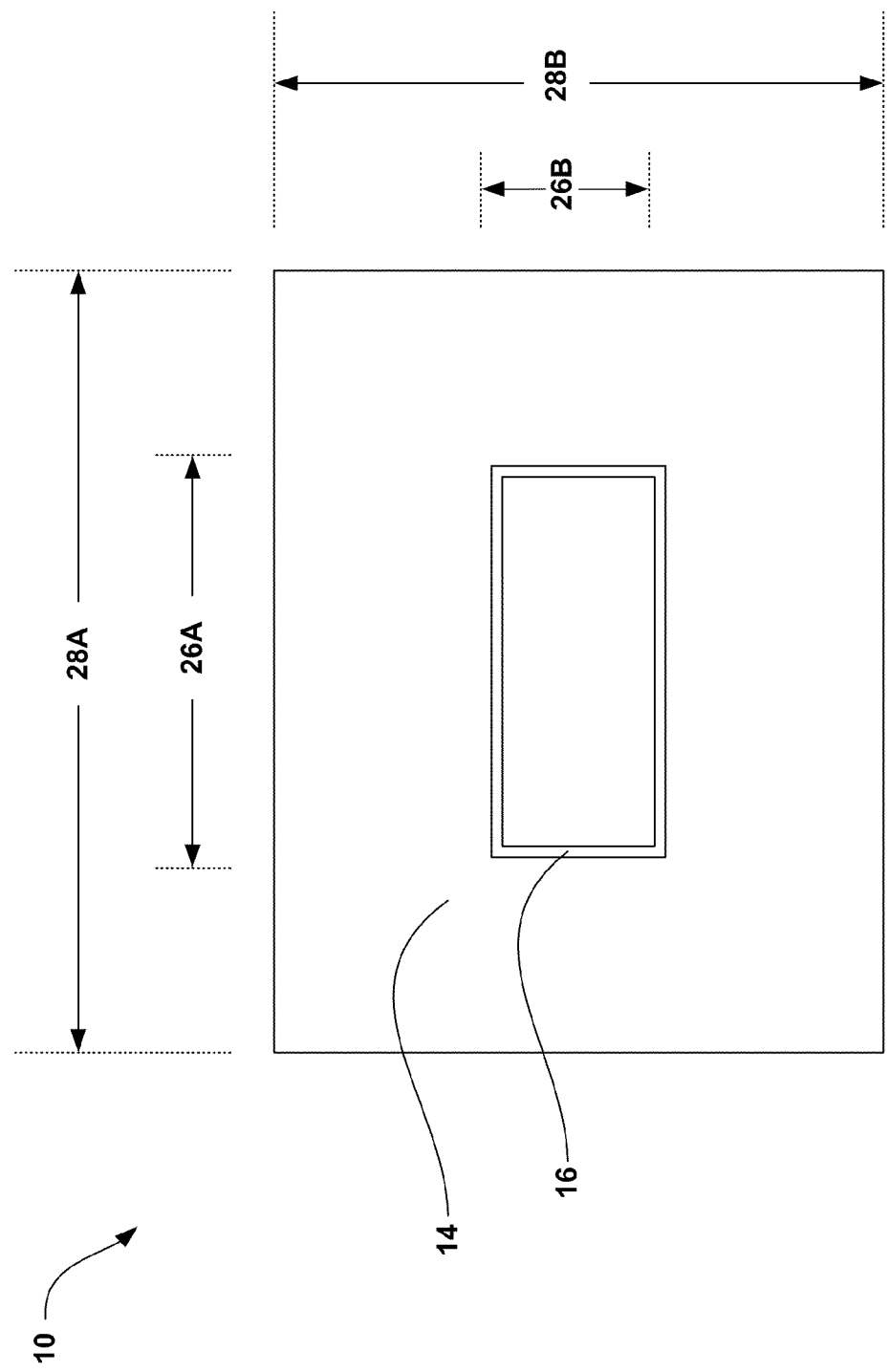
FIG. 3B is a cross-sectional top-view further illustrating the wearable ADR of FIG. 1, the cross section taken along line B-B' of FIG. 3A.

FIG. 3B is a cross-sectional top-view further illustrating wearable ADR 10 of FIG. 1, the cross section taken along line B-B' of FIG. 3A. As illustrated in FIG. 3B, housing 16 may also have a length 26A and width 26B, smaller dimensions for which may also allow greater comfort and unobtrusiveness of ADR 10 when worn by patient 12. Length 26A may be approximately 4.5 centimeters, and width 26B may be approximately 2.2 centimeters. A volume of housing 16 may be less than approximately 20 cubic centimeters, less than approximately 10 cubic centimeters, or approximately 6.3 cubic centimeters. These example dimensions for housing 16 may allow greater comfort and unobtrusiveness of ADR 10 when worn by patient 12. A length 28A and width 28B for bandage are also illustrated in FIG. 3B. Length 28A and width 28B may be within a range from approximately 6 centimeters to approximately 10 centimeters.

Figure 3C:
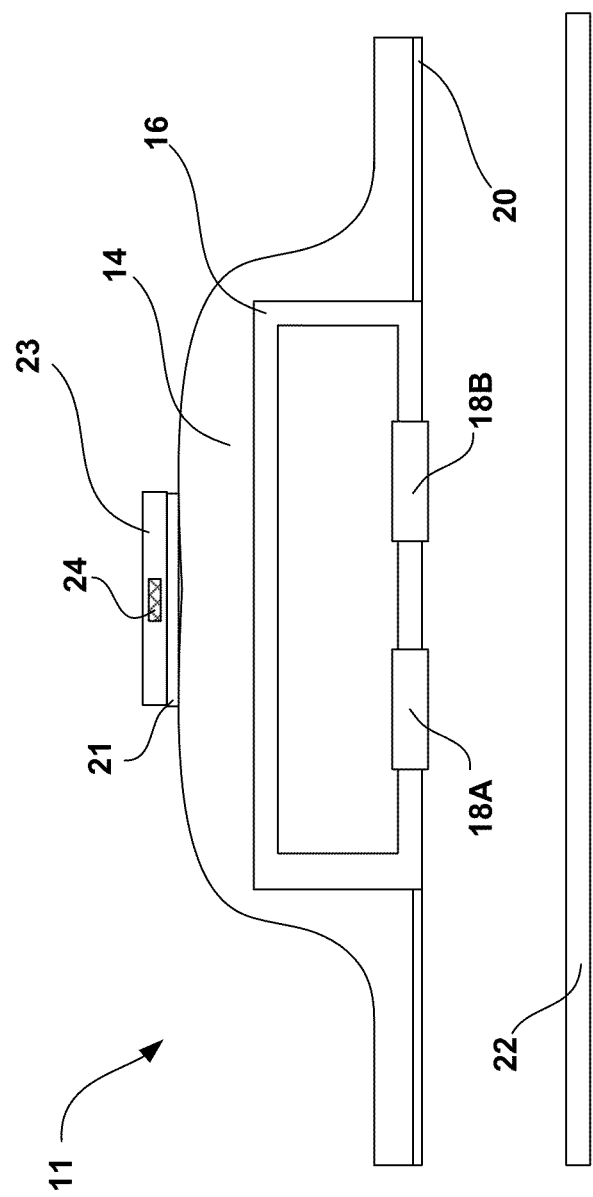
FIG. 3C is a cross-sectional side-view illustrating another example wearable ADR.

FIG. 3C is a cross-sectional side-view illustrating another example wearable ADR 11. ADR 11 is substantially similar to ADR 10 (FIG. 3A), and includes many substantially similar and like-numbered components as ADR 10. Such components are not discussed in detail with respect to FIG. 3C. However, unlike ADR 10, backing layer 22 does not include magnet 24 for ADR 11. Instead, magnet 24 is located within a different layer 23, which is attached to ADR 11, e.g., by an adhesive layer 21. In some embodiments, layer 23 is not required, and magnet 24 is attached directly to ADR 10 by adhesive layer 21 or other means.

The location of magnet 24 on ADR 11 may facilitate attachment of ADR 11 to patient 12 prior to power up or power on, and prior to posture sensor calibration. In particular, a clinician or patient 12 may remove backing layer 22, and attach ADR 11 to patient 12 either before or after the patient has assumed the predetermined posture. With ADR 11 attached and patient 12 in the predetermined posture, the user may remove backing layer 23 and magnet 24. In response to the removal, ADR 11 may power up or power on, and then calibrate the posture sensor in response to the removal and the powering up or on, either substantially immediately, or after a predetermined delay.

Further, the invention is not limited to the example embodiments illustrated in FIGS. 3A and 3C. For example, in some embodiments, a first magnet may be locating in backing layer 22, removal of which powers on or powers up the ADR, after which second magnet attached to the ADR may be removed to cause the ADR to calibrate the posture sensor. Additionally, as discussed above, a removable element is not limited to a magnet, need not be included within a backing layer, and need not be attached to an ADR by an adhesive.

Moreover, the invention is not limited to embodiments in which removal of an element causes power on/up or sensor calibration. In other embodiments, either or both of power on/up or posture sensor calibration may occur in response to different signals provided to an ADR. For example, movement of magnet not attached to the ADR proximate to the ADR, or "tapping" the ADR, which may be sensed via a piezoelectric element or accelerometer, may be cause the ADR to power on/up or calibrate a sensor.

Figure 4:
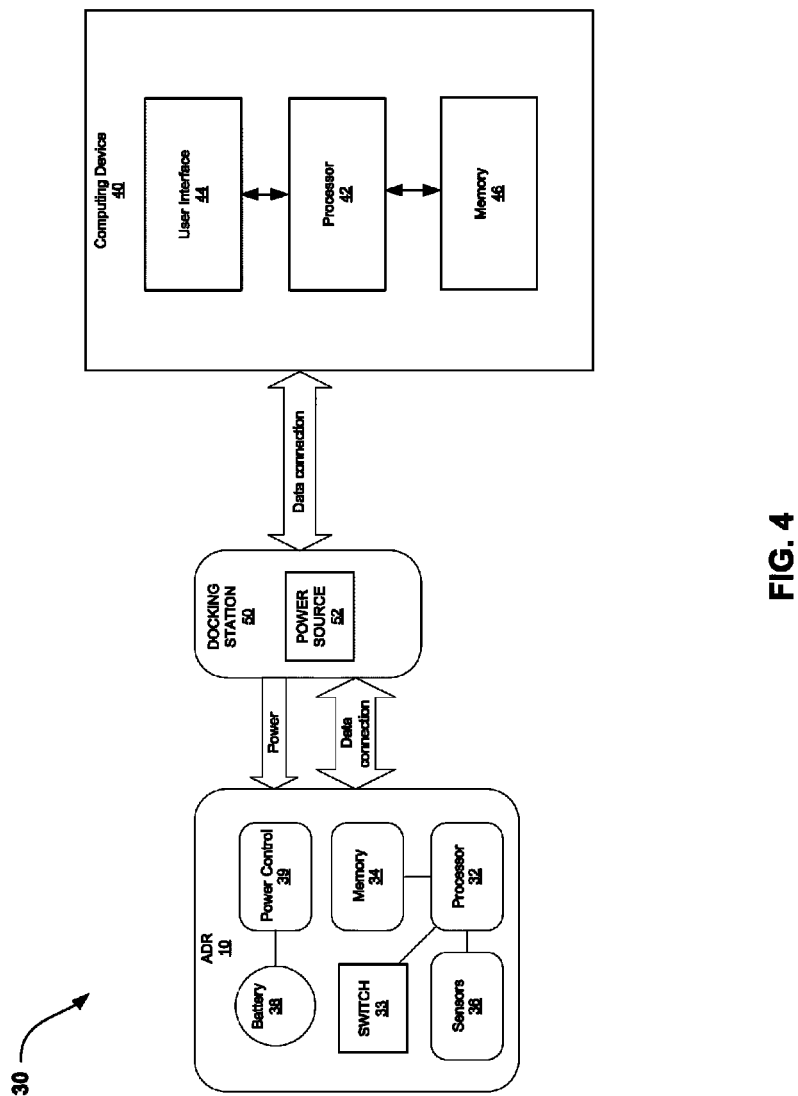
FIG. 4 is block diagram illustrating an example system that includes the wearable ADR of FIG. 1, and further illustrating the wearable ADR of FIG. 1.

FIG. 4 is block diagram illustrating an example system 30 that includes ADR 10. As shown in the example of FIG. 4, ADR 10 includes a variety of components that may be located on or within housing 16, such as a processor 32, switch 33, memory 34, sensors 36, internal power source 38, e.g., battery 38, and power control module 39. Sensors 36 may include one or more sensors as described below.

Processor 32 controls the operation of ADR 10 as instructed through instructions stored in memory 34. Processor 32 receives data produced by sensors 36 and conditions, filters, or samples the data before storing the processed data in memory 32. Processor 32 may include a microprocessor, a controller, a digital signal processor (DSP), an application specific integrated circuit (ASIC), a field-programmable gate array (FPGA), discrete logic circuitry, or the like. Memory 34 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. Memory 34 stores at least a portion of the data generated by sensors 36, as determined by processor 32. In some embodiments, memory 34 may also store program instructions that, when executed by processor 32, determine the operation of sensors 36, the processing of generated data, or the transfer of data to another device. In addition, memory 34 may store information related to any other function described herein.

Sensors 36 may include one or more individual sensors, where the sensors may include multiple of one type of sensor. Each of sensors 36 generates a signal as a function of one or more physiological or activity parameters of patient 12. Processor 32 or circuitry within sensors 36 may condition or processes the data generated by each sensor. For example, ADR 10 may include one or more analog to digital converters to convert analog signals generated by sensors 36 into digital signals usable by processor 32, as well as suitable filter and amplifier circuitry. Further, as illustrated in FIG. 4, sensors 36 may be located within housing 16 or on the surface of housing 16. In other embodiments, sensors 36 may include a sensor tethered to housing 16 through a lead or other similarly insulated conductive wire.

As discussed above, exemplary physiological parameters of patient 12 that may be monitored by ADR 10 to determine values of one or more quality of life metrics include activity level, posture, heart rate, respiration rate, blood oxygen saturation, partial pressure of oxygen within blood, EEG, ECG, partial pressure of oxygen within cerebrospinal fluid, muscular activity (EMG), temperature (such as skin temperature), and arterial blood flow of patient 12. Sensors 36 may be of any type known in the art capable of generating a signal as a function of one or more of these parameters. For example, sensors 36 may include one or more thermocouples or thermistors to detect temperature of patient 12. Alternatively, an optical sensor that generates a signal as a function of the partial pressure of oxygen within the cerebrospinal fluid may be included in sensors 36.

In some embodiments, in order to determine one or more sleep quality metric values, processor 32 determines when patient 12 is attempting to fall asleep by detecting that patient 12 is laying down and has not moved for a predetermine period of time. This posture detection may also be coupled with an ECG measurement or breathing rate measurement. ECG and or respiration rate may signal a sleeping event. For example, processor 32 may identify the time that patient begins attempting to fall asleep based on the generated data from sensors 36.

In other embodiments, ADR 10 may include one or more sensors 36 that generate a signal as a function of patient activity. For example, sensors 36 may include one or more accelerometers, gyros, mercury switches, or bonded piezoelectric crystals that generate a signal as a function of patient activity, e.g., body motion, footfalls or other impact events, and the like. The plurality of accelerometers, gyros, or magnetometers may be oriented orthogonally to generate signals which indicate the posture of patient 12. Processor 36 may identify a time when the activity level of patient 12 falls below a threshold activity level value stored in memory 34, and may determine whether the activity level remains substantially below the threshold activity level value for a threshold amount of time stored in memory 34. In other words, patient 12 remaining inactive for a sufficient period of time may indicate that patient 12 is attempting to fall asleep. If processor 32 determines that the threshold amount of time is exceeded, processor 32 may identify the time at which the activity level fell below the threshold activity level value as the time that patient 12 began attempting to fall asleep.

Processor 32 may also determine when patient 12 wakes up to store the length of time patient 12 was asleep. Sensors 36 may also determine the amount of activity during patient sleep, as more activity may be representative of lower quality of sleep for patient 12. This data may be useful to a physician and patient 12 as asking the patient to rate quality of sleep is highly subjective and not very accurate due to the fact that the patient was sleeping at the time.

When sensors 36 include accelerometers, for example, that are aligned in this manner, e.g., a multi-axis accelerometer, processor 32 may monitor the magnitude and polarity of DC components of the signals generated by the accelerometers to determine the orientation of patient 12 relative to the Earth's gravity, e.g., the posture of patient 12. In particular, the processor 32 may compare the DC components of the signals to respective threshold values stored in memory 34 to determine whether patient 12 is or is not recumbent. Further information regarding use of orthogonally aligned accelerometers to determine patient posture may be found in a commonly assigned U.S. Pat. No. 5,593,431, which issued to Todd J. Sheldon.

Processor 32 may periodically determine the posture of patient 12, and may store indications of the determined postures within memory 34. Where ADR 10 includes a plurality of orthogonally aligned accelerometers located on or within the trunk of patient 12, as illustrated in FIG. 1, processor 32 may be able to periodically determine whether patient is, for example, upright or recumbent, e.g., lying down.

Processor 32 may identify postures and posture transitions by comparing the signals generated by the accelerometers to one or more respective threshold values. For example, when patient 12 is upright, a DC component of the signal generated by one of the plurality of orthogonally aligned accelerometers may be substantially at a first value, e.g., high or one, while the DC components of the signals generated by the others of the plurality of orthogonally aligned accelerometers may be substantially at a second value, e.g., low or zero. When patient 12 becomes recumbent, the DC component of the signal generated by one of the plurality of orthogonally aligned accelerometers that had been at the second value when the patient was upright may change to the first value, and the DC components of the signals generated by others of the plurality of orthogonally aligned accelerometers may remain at or change to the second value. Processor 32 may compare the signals generated by such sensors to respective threshold values stored in memory 34 to determine whether they are substantially at the first or second value, and to identify when the signals change from the first value to the second value.

Processor 32 may determine an activity level based on one or more of the accelerometer signals by sampling the signals and determining a number of activity counts during the sample period. For example, processor 32 may compare the sample of a signal generated by an accelerometer to one or more amplitude thresholds stored within memory 34, and may identify each threshold crossing as an activity count. Where processor 32 compares the sample to multiple thresholds with varying amplitudes, processor 32 may identify crossing of higher amplitude thresholds as multiple activity counts. Using multiple thresholds to identify activity counts, processor 32 may be able to more accurately determine the extent of patient activity for both high impact, low frequency and low impact, high frequency activities. Processor 32 may store the determined number of activity counts in memory 34 as an activity level. In some embodiments, processor 46 may apply a digital filter, that passes a band of the accelerometer signal from approximately 0.1 Hz to 10 Hz, e.g., the portion of the signal that reflects patient activity.

Processor 32 may identify postures and record activity levels continuously or periodically, e.g., one sample of the signals output by sensors 36 every minute or continuously for ten minutes each hour. Further, processor 32 need not identify postures and record activity levels with the same frequency. For example, processor 32 may identify postures less frequently then activity levels are determined.

In some embodiments, processor 32 limits recording of postures and activity levels to relevant time periods, i.e., when patient 12 is awake or likely to be awake, and therefore likely to be active. In other embodiments, processor 32 may maintain a real-time clock, and may record posture events based on the time of day indicated by the clock, e.g., processor 32 may limit posture event recording to daytime hours. Alternatively, processor 32 may wirelessly interact with a real-time clock within a patient programmer.

In some embodiments, processor 32 may monitor one or more physiological parameters of patient 12 via signals generated by sensors 36, and may determine when patient 12 is attempting to sleep or asleep based on the physiological parameters. For example, processor 32 may determine when patient 12 is attempting to sleep by monitoring the posture of patient 12 to determine when patient 12 is recumbent.

In order to determine whether patient 12 is asleep, processor 32 may monitor any one or more physiological parameters that discernibly change when patient 12 falls asleep, such as activity level, heart rate, EEG, ECG morphological features, respiration rate, respiratory volume, blood pressure, blood oxygen saturation, partial pressure of oxygen within blood, muscular activity and tone, skin temperature, arterial blood flow, eye motion, and galvanic skin response. Processor 32 may additionally or alternatively monitor the variability of one or more of these physiological parameters, such as heart rate and respiration rate, which may discernible change when patient 12 is asleep. In some embodiments, processor may determine a probability of sleep for each of a plurality of parameters, and combine the probabilities to determine an overall probability that indicates whether the patient is asleep. Further details regarding monitoring physiological parameters to identify when a patient is attempting to sleep and when the patient is asleep may be found in a commonly-assigned and co-pending U.S. patent application by Kenneth Heruth and Keith Miesel, entitled "DETECTING SLEEP," which was assigned Ser. No. 11/081,786 and filed Mar. 16, 2005, and is incorporated herein by reference in its entirety.

Although described above with reference to an exemplary embodiment in which sensors 36 include accelerometers, the sensors may include any of a variety of types of sensors that generate signals as a function of patient posture and/or activity. For example, sensors 36 may include orthogonally aligned gyros or magnetometers that generate signals that indicate the posture of patient 12.

Other sensors 36 that may generate a signal that indicates the posture of patient 12 include electrodes that generate an electromyogram (EMG) signal, or bonded piezoelectric crystals that generate a signal as a function of contraction of muscles. Such sensors 36 may be placed on the legs, buttocks, abdomen, or back of patient 12, as described above. The signals generated by such sensors when placed at these locations may vary based on the posture of patient 12, e.g., may vary based on whether the patient is standing, sitting, or lying down.

Other sensors 36 that output a signal as a function of patient activity may include one or more bonded piezoelectric crystals, mercury switches, or gyros that generate a signal as a function of body motion, footfalls or other impact events, and the like. Additionally or alternatively, sensors 36 may include one or more electrodes that generate an electromyogram (EMG) signal as a function of muscle electrical activity, which may indicate the activity level of a patient. The electrodes may be, for example, located on the legs, abdomen, chest, back or buttocks of patient 12 to detect muscle activity associated with walking, running, or the like. The electrodes may instead be located on the head to detect EEG signals or over the chest to detect ECG signals. Any electrical signals may detected by two or more electrodes included in sensors 36. The electrodes may be attached to housing 16 or located on an adhesive portion of ADR 10 or tethered to housing 16.

Further, in some embodiments, processor 32 may monitor one or more signals that indicate a physiological parameter of patient 12, which in turn varies as a function of patient activity. For example, processor 32 may monitor a signal that indicates the heart rate, ECG morphology, respiration rate, subcutaneous temperature, or muscular activity of the patient, and sensors 36 may include any known sensors that output a signal as a function of one or more of these physiological parameters. In such embodiments, processor 32 may periodically determine a heart rate, value of an ECG morphological feature, respiration rate, or muscular activity level of patient 12 based on the signal. The determined values of these parameters may be mean or median values. In some embodiments, respiratory rate may also be used to show signs of sleep apnea or other sleep disorders that cause patient 12 to stop breathing for a certain period of time.

In alternative embodiments, processor 32 compares a determined value of such a physiological parameter to one or more thresholds or a look-up table stored in memory to determine a number of activity counts, and stores the determined number of activity counts in memory 34 as a determined activity level. In other embodiments, processor 32 may store the determined physiological parameter value as a determined activity level. The use of activity counts, however, may allow processor 32 to determine an activity level based on a plurality of signals generated by a plurality of sensors 36. For example, processor 32 may determine a first number of activity counts based on a sample of an accelerometer signal and a second number of activity counts based on a heart rate determined from an electrogram signal at the time the accelerometer signal was sampled. Processor 32 may determine an activity level by calculating the sum or average, which may be a weighted sum or average, of first and second activity counts. In some embodiments, processor 32 may not interact with previously stored data in order to reduce the amount of power drained from battery 38.

Sensors 36 may also include optical pulse oximetry sensors or Clark dissolved oxygen sensors located within, as part of a housing of, or outside of ADR 10, which generate signals as a function of blood oxygen saturation and blood oxygen partial pressure respectively.

In some embodiments, sensors 36 may include one or more external flow sensors positioned to generate a signal as a function of arterial blood flow. A flow sensor may be, for example, an electromagnetic, thermal convection, ultrasonic-Doppler, or laser-Doppler flow sensor. Further, in some external medical device embodiments of the invention, sensors 36 may include one or more electrodes positioned on the skin of patient 12 to generate a signal as a function of galvanic skin response.

Processor 32 may also detect arousals and/or apneas that occur when patient 12 is asleep based on one or more of the above-identified physiological parameters. For example, processor 32 may detect an arousal based on an increase or sudden increase in one or more of heart rate, heart rate variability, respiration rate, respiration rate variability, blood pressure, or muscular activity as the occurrence of an arousal. Processor 32 may detect an apnea based on a disturbance in the respiration rate of patient 12, e.g., a period with no respiration. Memory 34 may store thresholds used by processor 46 to detect arousals and apneas. Processor 32 may determine, as a sleep quality metric value, the number of apnea events and/or arousals during a night.

Further, in some embodiments, processor 32 may determine which sleep state patient 12 is in during sleep, e.g., REM, S1, S2, S3, or S4, based on one or more of the monitored physiological parameters. In particular, memory 34 may store one or more thresholds for each of sleep states, and processor 32 may compare physiological parameter or sleep probability metric values to the thresholds to determine which sleep state patient 12 is currently in. Processor 32 may determine, as sleep quality metric values, the amounts of time per night spent in the various sleep states. As discussed above, inadequate time spent in deeper sleep states, e.g., S3 and S4, is an indicator of poor sleep quality. Consequently, in some embodiments, processor 32 may determine an amount or percentage of time spent in one or both of the S3 and S4 sleep states as a sleep quality metric.

Processor 32 may store any of these metric values and other physiological parameter data determined based on signals received from sensors 36 in memory 34. A computing device 40 may retrieve the physiological parameter data from ADR 10 via a wired or wireless connection with the ADR, e.g., a wired or wireless serial data connection. Computing device 40 may include a user interface 44, such as a display, to present the retrieved physiological parameter data to a user, and a memory 46 to store the data.

Processor 42 may format or otherwise process the data prior to presentation. For example, processor 42 may arrange the data as one or more timing diagrams, histograms, or the like. Processor 42 and memory 46 may include components similar to those listed above for processor 32 and memory 34, although the components within computing device 40 may generally by larger and more complex than those in the ADR.

The internal power source, e.g., battery 38, of ADR 10 may be primary or rechargeable, and may have, as an example, a Lithium Ion chemistry. Under the direction of processor 32, a power control module 39 may control recharging of battery 38, monitoring parameters of the battery for end-of-life estimations, and delivery of power from battery 38 to the other components of ADR 10. Power control module 39 may include circuitry known in the art for such functions, and may also include a switch to couple battery to the other components when a magnet 24 is removed from proximity to ADR 10, as described above.

Also, ADR 10 may include an additional switch 33 or other detection element for detecting removal of a magnet or some other signal to perform a posture sensor calibration. Switch 33 may be included in ADR 10 in embodiments in which the ADR is shipped or otherwise provided to a user in a fully-powered state, or in which separate magnets, removable elements, or other signals are used to control power on/up and sensor calibration.

Further, as shown in FIG. 4, system 30 may also include a docking station 50, which may facilitate the data communication between ADR 10 and computing device 40. The data connections between ADR and docking station, and docking station and computing device, may be wired or wireless serial or parallel data connections. Docking station 50 also may include or be coupled to an external power source 52, such as a battery or wall-outlet, for recharging battery 38 of ADR 10, or powering ADR 10. Docking station may, but need not, physically receive ADR or a portion thereof for transfer of data, recharging, or powering.

Figure 5:
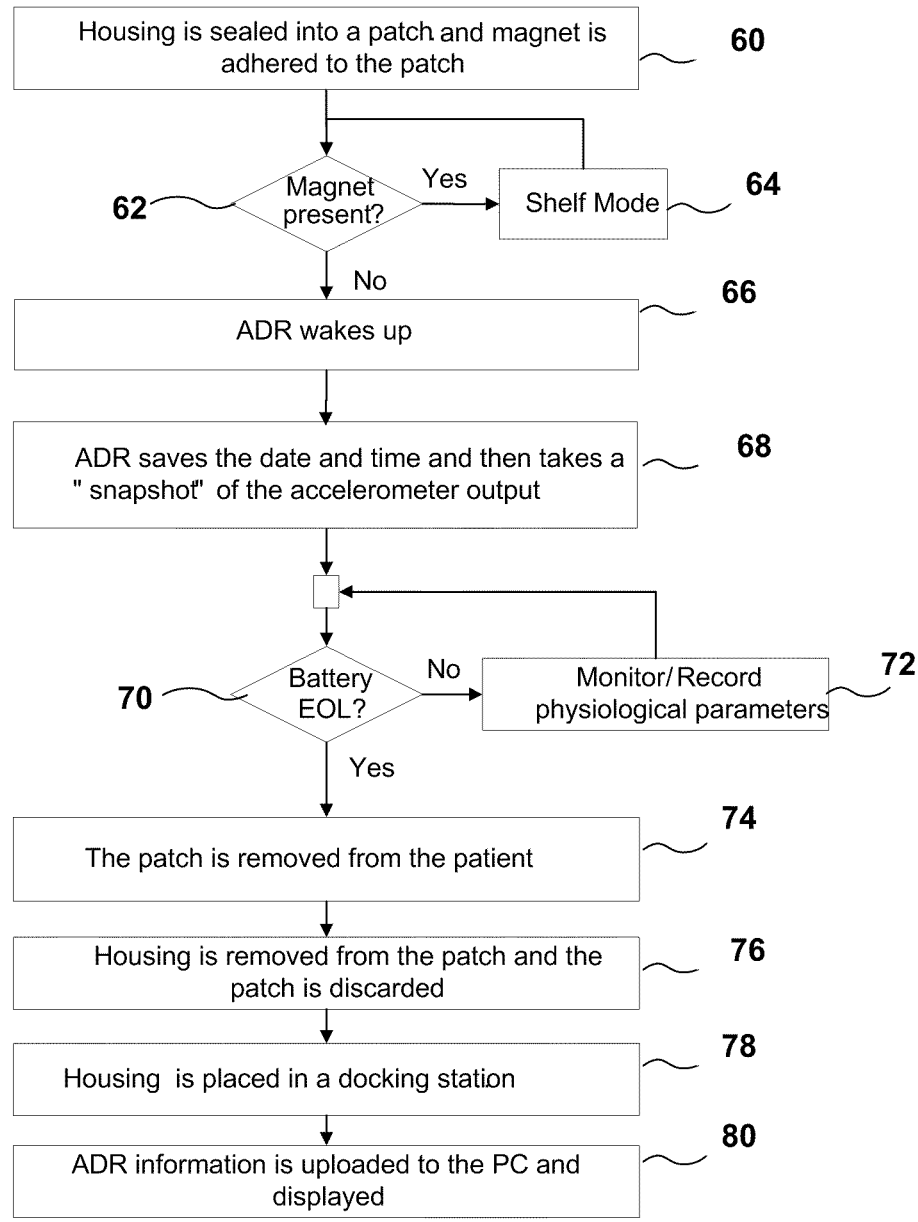
FIG. 5 is a flow diagram illustrating an example method for operating a wearable ADR according to the invention.

FIG. 5 is a flow diagram illustrating an example method for operating wearable ADR 10 according to the invention. Prior to use, e.g., during manufacturing, housing 16 with components therein or thereon is sealed into a patch, and a layer with a magnet is attached to an adhesive layer (60). ADR 10 detects the presence of the magnet (62), and remains in a "shelf mode," e.g., a no or low-power mode, so long as magnet is present (64). When ADR 10 detects removal of the magnet (62), ADR "wakes up," e.g., enters a powered or fully-functional mode (66). Removal of the magnet and back layer may be for attachment of the ADR to the patient, or after such attachment, as discussed above.

ADR 10 may then calibrate posture sensing, in embodiments with posture sensors, and start recording physiological parameter data (68). Calibrating posture sensing may include determining the orientation of the ADR with respect to the patient. For example, the user, e.g., clinician, may have patient 12 assume a predetermined position, e.g., lying down while face up, or upright, prior to removal of magnet 24. Processor 32 of ADR 10 may calibrate posture sensing by correlating the current output of the multi-axis accelerometers of sensors 36, e.g., upon power on/up or a predetermined delay thereafter, with the predetermined posture.

In some embodiments, as discussed above, the indication to calibrate posture sensing may be separate from the indication to power up or on, e.g., may be a later "start recording" indication. The "start recording" indication may take the form of removal of a magnet or backing layer, or a predetermined number or pattern of "taps" on ADR 10 by a user. Processor 32 of ADR 10 may detect such an indication via, for example, accelerometers included within sensors 36.

In some embodiments, as discussed above, the internal power source, e.g., battery 38, of ADR 10 may be rechargeable. In other embodiments, the internal power source need not be recharged. Further, in some embodiments, ADR 10 may monitor physiological parameters and record physiological parameter data (74) until a time determined based on the estimated end-of-service (EOS) of the power source (72). In such embodiments, processor 32 of ADR 10 may monitor a parameter, e.g., voltage or current, associated with the power source, and estimate the EOS based on the parameter.

When the end of monitoring time determined based on the estimated EOS is reached, processor 32 may end data recording, and prompt a patient to make the data recorder available for retrieval of information based on the estimation. For example, the patient may be prompted to return the ADR to a physician. The patient or physician may remove ADR 10 from patient 12 (76), remove housing 16 from bandage 14 (78), and place housing 16 into docking station 50 (80). Computing device 40 may then retrieve stored physiological parameter information from ADR 10 via docking station 50, as described above (82). In some embodiments, docking station 50 may power ADR during data transfer. Powering ADR 10 via docking station 50 during data transfer may be advantageous, particularly if ADR 10 has reached the EOS of its internal power source during data collection.

Figure 6:
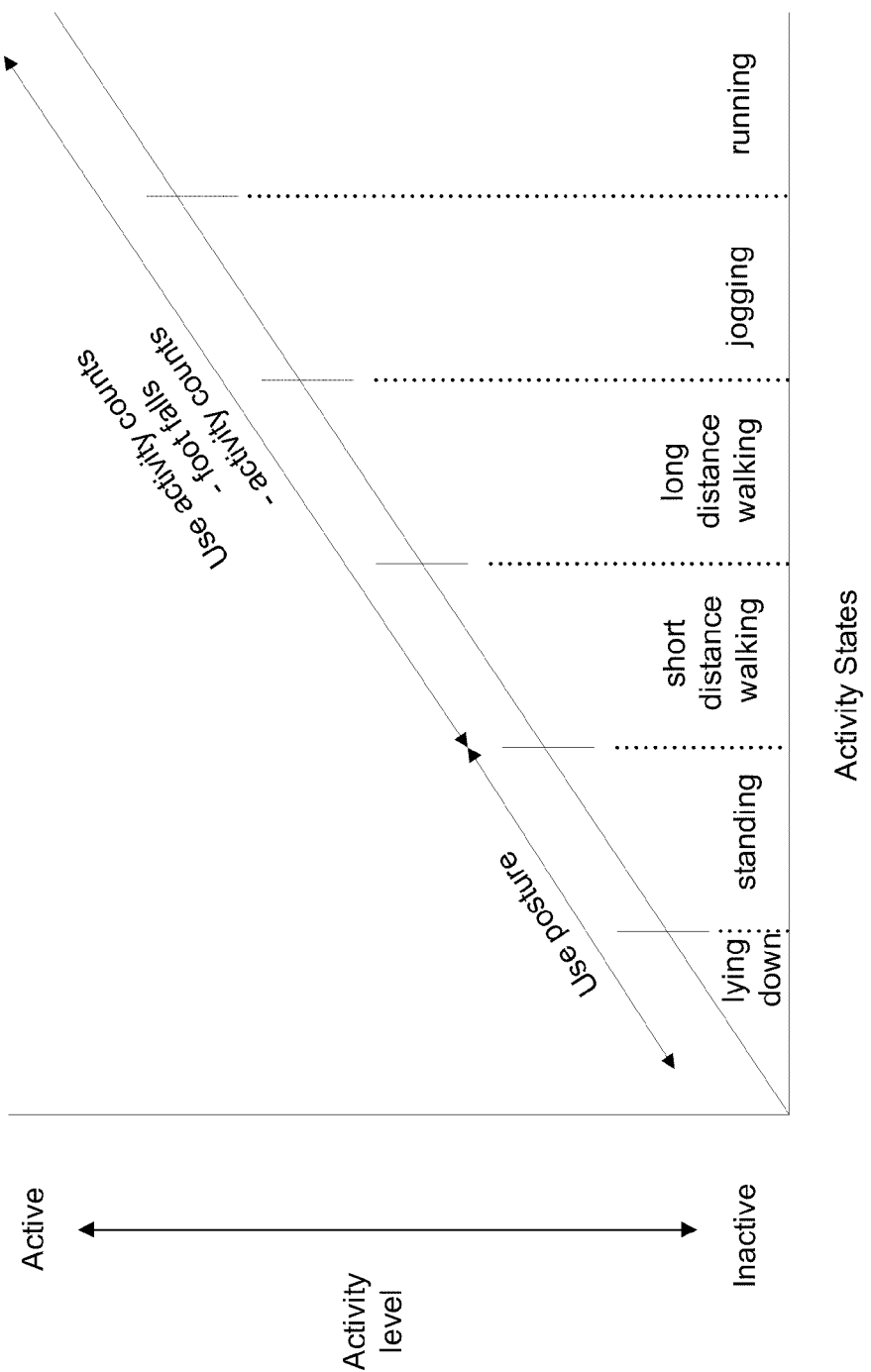
FIG. 6 is a graph illustrating an example relationship between posture and activity.

FIG. 6 is a graph illustrating an example relationship between posture and activity. At any moment in time, a patient can be thought of as being somewhere in an activity continuum. ADR 10 may use sensors 36 to determine how active a person is, this level of activity could be used to determine therapy efficacy and quality of life or provide closed loop therapy adjustment. Based solely on activity, different activity states could be determined such as short distance walking, long distance walking, jogging, and running If posture is gathered in addition to activity data, additional activity states such as lying down and standing can be determined to increase the resolution of the activity continuum as shown in FIG. 6. ADR 10 may record the number or length of times patient 12 spends above various activity thresholds, or within various activity states or postures, as activity and posture metrics, e.g., as physiological parameter data.

Figure 7:
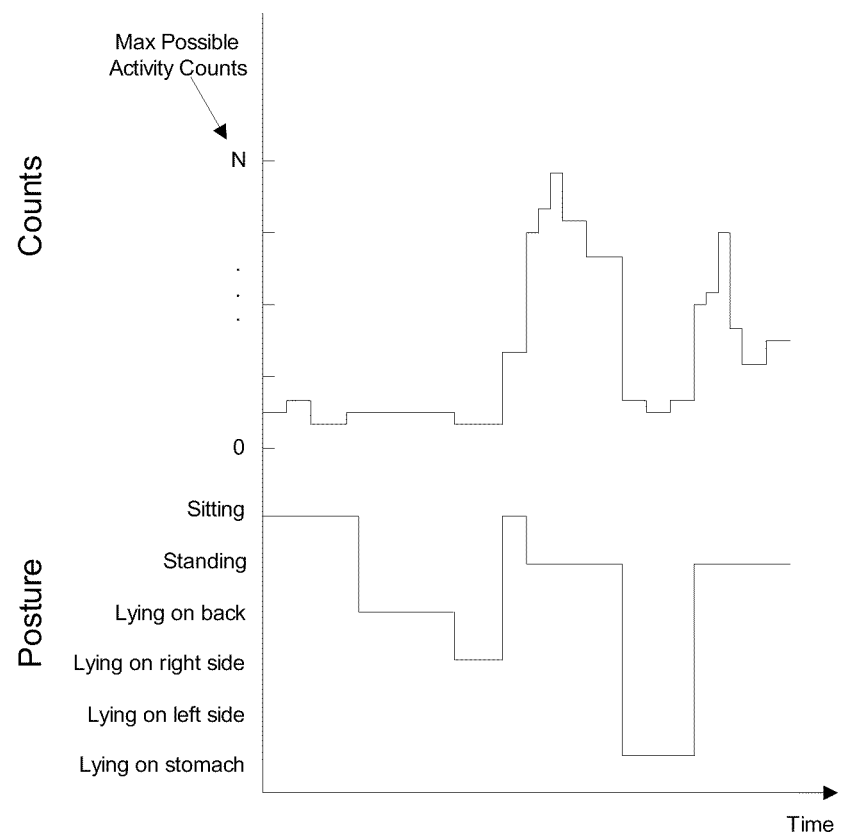
FIG. 7 is a timing diagram illustrating example physiological parameter data collected by a wearable ADR.

FIG. 7 is a timing diagram illustrating example physiological parameter data collected by a wearable ADR, such as ADR 10. As shown in FIG. 7, ADR 10 may use sensors 36, e.g., multi-axis accelerometers, to identify when patient 12 has reached or exceeded particular gross activity level thresholds, and is within particular postures. Processor 32 of ADR 10 may store such information as activity and posture metrics, respectively, for later retrieval by a computing device.

Figure 8:
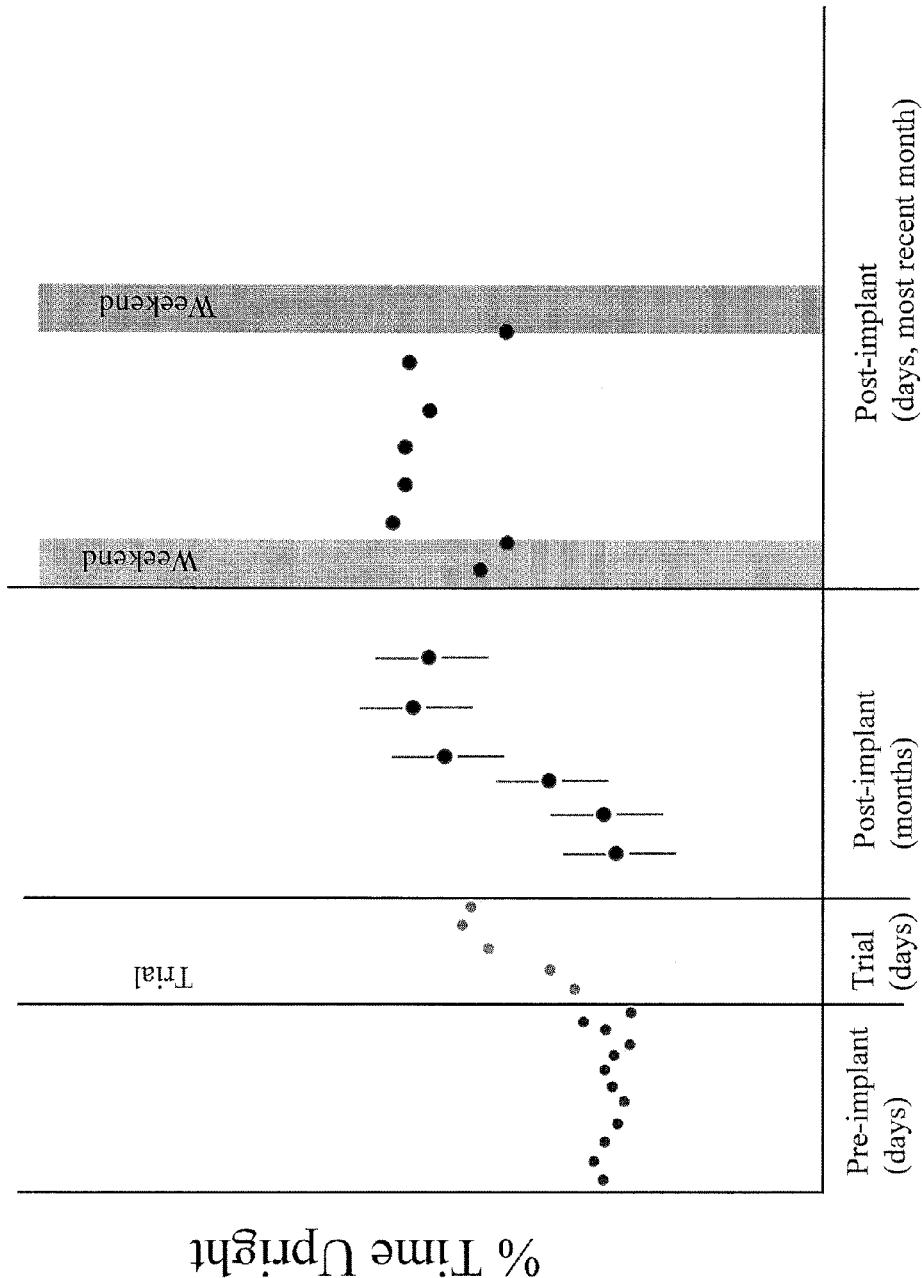
FIG. 8 is a histogram illustrating an example presentation of physiological parameter data collected by a wearable ADR.

FIG. 8 is a histogram illustrating an example presentation of physiological parameter data collected by a wearable ADR, such as ADR 10. The example presentation of FIG. 8 may be, for example, displayed by computing device 40 via user interface 44 after processing physiological parameter data received from ADR 10. FIG. 8 illustrates a single example posture metric, percent of time in upright positions, over time.

As shown in FIG. 8, ADR 10 may be used to evaluate the posture metric during a variety of time periods, including a baseline evaluation pre-therapy, an evaluation during a trialing period, and an evaluation post-implant. Reviewing such a histogram may provide a user with an objective indication of the effectiveness of the therapy during trialing prior to implanting a medical device, and an objective evaluation of the continuing effectiveness of the therapy post implant. Such information may also allow the user to identify any gradual or sudden changes in the condition of the patient over time.

Figure 9:
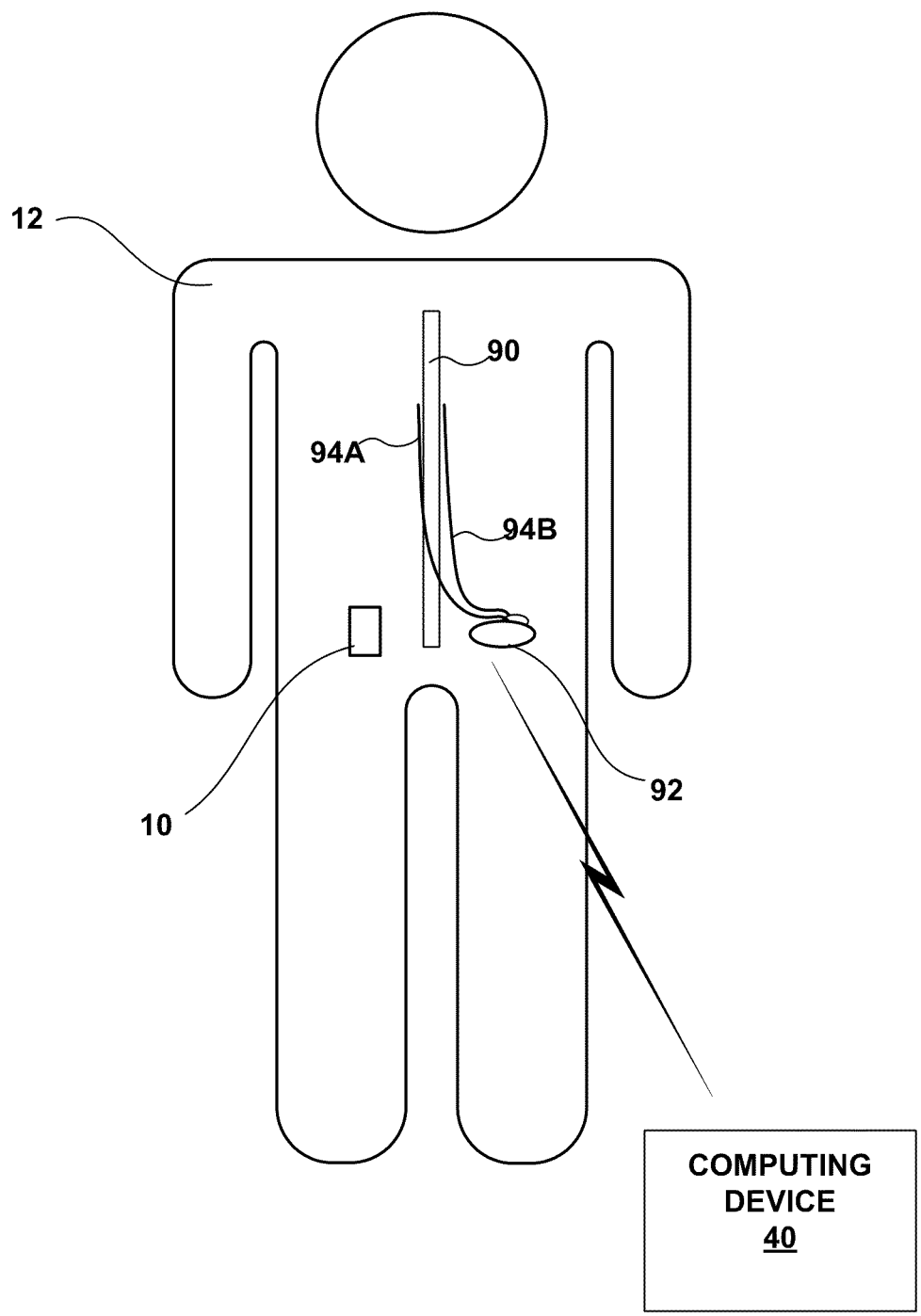
FIG. 9 is a conceptual diagram illustrating the wearable ADR and patient of FIG. 1 in conjunction with an implantable medical device implanted within the patient.

FIG. 9 is a conceptual diagram illustrating the wearable ADR 10 and patient 12 of FIG. 1 in conjunction with an implantable medical device (IMD) 92 implanted within the patient. In the illustrated embodiment, IMD 92 is an implantable neurostimulator that delivers stimulation therapy to a spinal cord 90 of patient 12, e.g., spinal cord stimulation (SCS), via leads 94A and 94B (collectively, "leads 94"). However, the invention is not limited to any particular therapy, or to implanted devices. For example, ADR 10 may be used to record physiological parameter data during delivery of therapy by an external device, such as an external trial neurostimulator or other external trial device. As discussed above, ADR 10 may record physiological parameter data during delivery of therapy by IMD 92 to evaluate the effectiveness of the delivery of therapy by the IMD.

IMD 92 may deliver therapy according to therapy parameter sets. In stimulation embodiments, a therapy parameter set may include voltage or current pulse amplitude, as well as pulse width and rate. Further, the therapy parameter sets may include respective combinations of electrodes (not shown) carried by leads 94. For other therapies, the content of a parameter set may be different. For example, a parameter set for a drug pump may include a titration rate and duty cycle. As illustrated in FIG. 9, in addition to computing with ADR 10 to retrieve physiological parameter data, as discussed above, computing device 40 may communicate with IMD 92, e.g., via wireless telemetry. Computing device 40 may communicate with IMD 92 to, for example, retrieve information regarding the therapy parameter sets used by the IMD to delivery therapy to patient 12.

Figure 10:
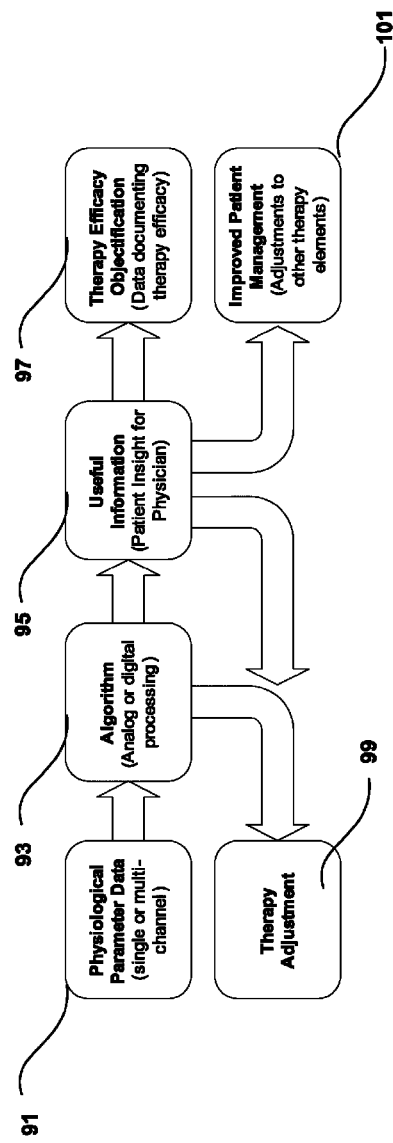
FIG. 10 is a flow diagram illustrating example use of physiological parameter data collected by a wearable ADR.

FIG. 10 is a flow diagram illustrating example use of physiological parameter data collected by a wearable ADR, such as ADR 10. As shown in FIG. 10, the ADR may record physiological parameter data for one or more sensed physiological parameters during delivery of therapy, as discussed herein (91). The data may be processed by the ADR, the therapy delivering medical device, a special purpose programming device or other computing device, or some other device, by application of an algorithm or other analog or digital signal processing techniques (93). For example, the processing may yield values of one or more sleep quality, activity, or posture metrics, as described herein.

The therapy delivering medical device, independently or as controlled be another device, may deliver therapy based on such processed data (99). Physiological parameter data from the ADR, whether or not further processed, may be used by the medical device, or another device controlling the medical device, to provide closed loop therapy. Further, whether alone or combined with subjective information from the patient, such information may be used to control or inform decisions regarding other therapies (101), or to objectively evaluate the efficacy of the therapy delivered to the patient by the medical device during data collection by the ADR (97). Subjective information from the patient may include information logged into a patient diary through interaction of the patient with a programming or other computing device, which may prompt the patient to respond to queries regarding quality of life or therapy efficacy. Objective therapy evaluation based on physiological parameter data from an ADR is described in greater detail below.

Figure 11:
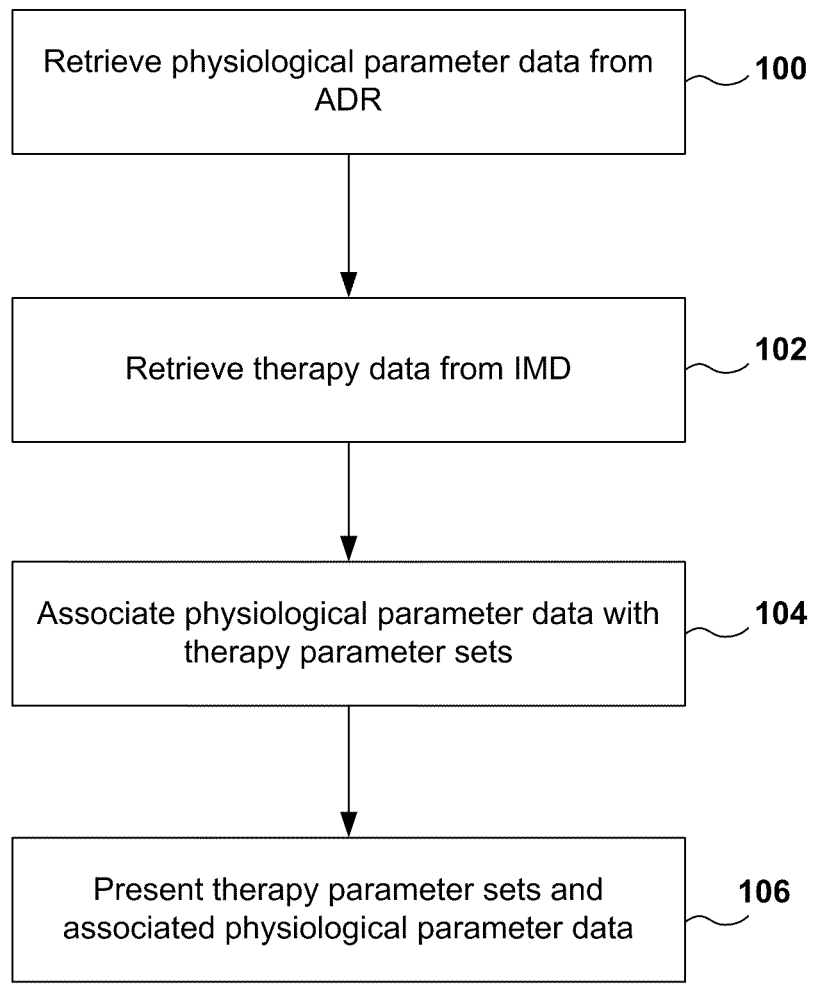
FIG. 11 is a flow diagram illustrating an example technique for associating physiological parameter data collected by a wearable ADR with therapy data relating to therapy delivered by a medical device.

FIG. 11 is a flow diagram illustrating an example technique for associating physiological parameter data collected by a wearable ADR with therapy data relating to therapy delivered by a medical device. The example technique of FIG. 11 may be employed by, for example, computing device 40.

Computing device 40 may retrieve physiological parameter data from ADR 10, as described above (100). IMD 92 or an associated programming device may record therapy changes over time as therapy data. Computing device 40 may also retrieve therapy data from IMD 92 or the programming device (102). Each therapy parameter change may represent a change to a new parameter set or a parameter set selected from a plurality of preprogrammed sets. Computing device 40 may associate the physiological parameter data and therapy data according to time, e.g., may associate each parameter set with physiological parameter data collecting during delivery of therapy according to the parameter set (104). The computing device may present therapy data, e.g., parameter sets, and associated physiological parameter data to a user (104). The computing device may, for example present therapy data and associated physiological parameter data to the user in tabular or graphical form via a display. The user may objectively evaluate the relative efficacy of the therapy changes or parameter sets based on the physiological parameter data associated with the change or set.

Figure 12:
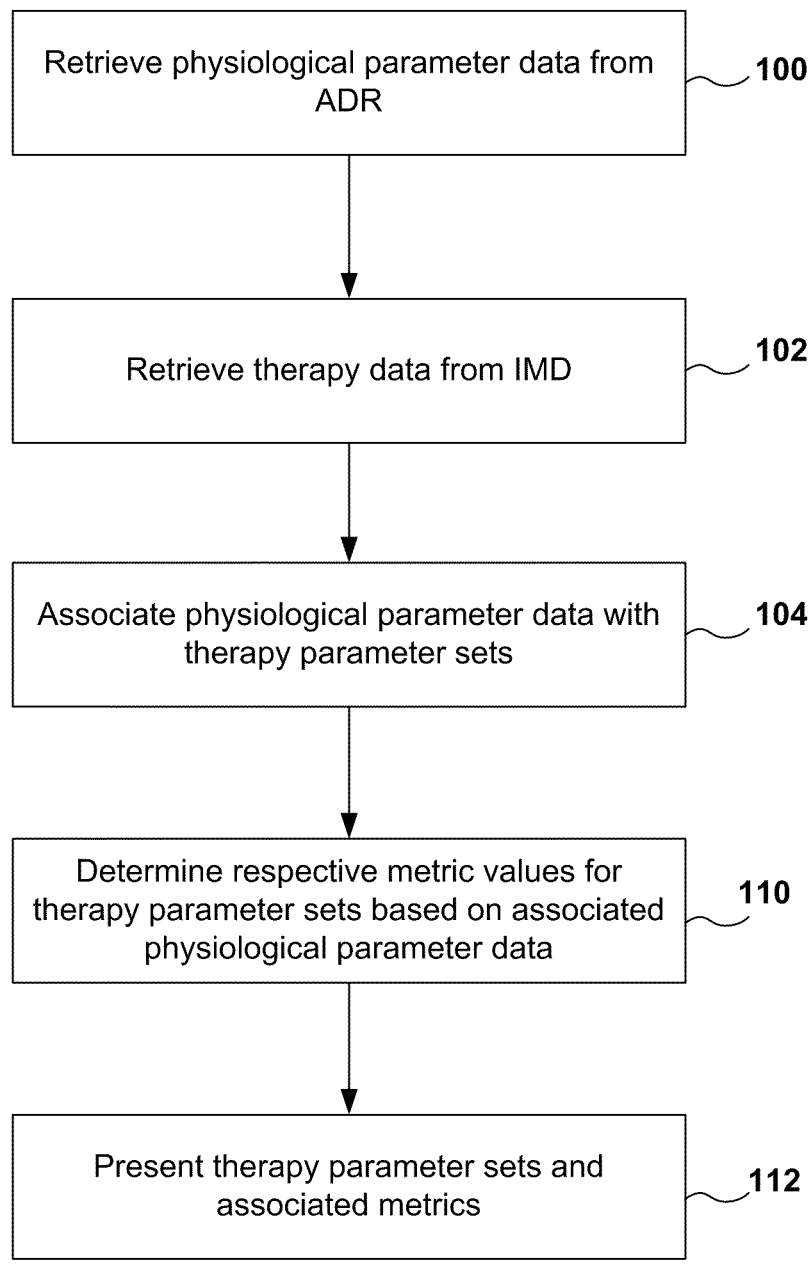
FIG. 12 is a flow diagram illustrating an example technique for determining quality of life metric values for each of a plurality of therapy parameter sets used by a medical device that delivers therapy based on physiological parameter data collected by a wearable ADR.

FIG. 12 is a flow diagram illustrating an example technique for determining quality of life metric values for each of a plurality of therapy parameter sets used by a medical device that delivers therapy based on physiological parameter data collected by a wearable ADR. The technique of FIG. 12 may be employed by, for example, computing device 40. According to the illustrated technique, the computing device retrieves physiological parameter data from the ADR and therapy data from the IMD, and associates the physiological parameter data with whichever therapy parameter set was active during it collection, as described above with reference to the FIG. 11 (100-104). The computing device may then further determine respective values for one or more quality of life metrics for each of the therapy parameter sets based on the physiological parameter data associated with the therapy parameter sets (110). The computing device may present a plurality of parameter sets and associated values of any one or more metrics to a user (112).

The quality of life metrics may be sleep quality metrics, activity metrics, or posture metrics. In general, the computing device determines sleep quality metrics by determining whether the patient is asleep or within a particular sleep state. The computing device may determine when the patient was asleep by analyzing data from the ADR, including data from any of the sensors described above as being useful to determine whether the patient is asleep or within a particular sleep state. The computing device may determine values for activity and posture metrics by analyzing recorded data from any sensors of ADR described above as generating signals indicative of gross motor activity, cardiovascular activity, muscular activity or posture. The computing device or ADR may compare such signals to thresholds to determine activity levels and postures.

Sleep efficiency and sleep latency are example sleep quality metrics for which a computing device may determine values. Sleep efficiency may be measured as the percentage of time while the patient is attempting to sleep that the patient is actually asleep. Sleep latency may be measured as the amount of time between a first time when the patient begins attempting to fall asleep and a second time when the patient falls asleep, and thereby indicates how long a patient requires to fall asleep.

The time when the patient begins attempting to fall asleep may be determined in a variety of ways. For example, the ADR or medical device may receive an indication from the patient that the patient is trying to fall asleep. In other embodiments, the computing device may determine when the patient is attempting to fall asleep based on the activity level or posture of the patient as indicated by physiological parameter data received from the ADR Other sleep quality metrics that may be determined include total time sleeping per day, the amount or percentage of time sleeping during nighttime or daytime hours per day, and the number of apnea and/or arousal events per night. In some embodiments, which sleep state the patient is in, e.g., rapid eye movement (REM), or one of the nonrapid eye movement (NREM) states (S1, S2, S3, S4) may be determined based on physiological parameters monitored by the medical device, and the amount of time per day spent in these various sleep states may be a sleep quality metric. Because they provide the most "refreshing" type of sleep, the amount of time spent in one or both of the S3 and S4 sleep states, in particular, may be determined as a sleep quality metric.

An activity metric value may be, for example, a mean or median activity level, such as an average number of activity counts per unit time. In other embodiments, the computing device may choose an activity metric value from a predetermined scale of activity metric values based on comparison of a mean or median activity level to one or more threshold values. The scale may be numeric, such as activity metric values from 1-10, or qualitative, such as low, medium or high activity. In some embodiments, the computing device compares each activity level indicated by the data from the ADR that has been associated with a therapy parameter set with the one or more thresholds, and determines percentages of time above and/or below the thresholds as one or more activity metric values for that therapy parameter set. In other embodiments, each activity level associated with a therapy parameter set is compared with a threshold, and an average length of time that consecutively determined activity levels remain above the threshold is determined as an activity metric value for that therapy parameter set.

A posture metric value may be, for example, an amount or percentage of time spent in a posture while a therapy parameter set is active, e.g., average amount of time over a period of time, such as an hour, that a patient was within a particular posture. In some embodiments, a posture metric value may be an average number of posture transitions over a period of time, e.g., an hour, that a particular therapy parameter sets was active.

FIGS. 13-15 are conceptual diagrams illustrating presentation of various example quality of life metric values associated with therapy parameter sets to a user. More particularly, FIG. 13 illustrates an example list or table 120 of therapy parameter sets and associated sleep quality metric values that may be presented to a clinician by, as examples computing device 40 or a specialized programming device for a therapy delivering medical device. Each row of example list 120 includes an identification of one of therapy parameter sets, the parameters of the set, and a representative value for one or more sleep quality metrics associated with the identified therapy parameter set, such as sleep efficiency, sleep latency, or both. The example list 120 includes representative values for sleep efficiency, sleep latency, and "deep sleep," e.g., the average amount of time per night spent in either of the S3 and S4 sleep states.

FIG. 14 illustrates an example list 130 of therapy parameter sets and associated activity metric values that may be presented to a clinician by, as examples computing device 40 or a specialized programming device for a therapy delivering medical device. Each row of example list 130 includes an identification of one of the therapy parameter sets, the parameters of the therapy parameter set, and values associated with the therapy parameter set for each of two illustrated activity metrics.

The activity metrics illustrated in FIG. 14 are a percentage of time active, and an average number of activity counts per hour. The computing or other device may determine the average number of activity counts per hour for one of the illustrated therapy parameter sets by identifying the total number of activity counts associated with the parameter set and the total amount of time that the IMD or other therapy-delivering medical device was using the parameter set. The computing or other device may determine the percentage of time active for one of parameter sets by comparing activity levels over time as indicated by the data recorded by ADR to an "active" threshold, and determining the percentage of activity levels above the threshold. As illustrated in FIG. 14, the computing device may also compare each activity level to an additional, "high activity" threshold, and determine a percentage of activity levels above that threshold.

Similarly, FIG. 15 illustrates an example list 140 of therapy parameter sets and associated posture metric values that may be presented by the computing device or some other device. The posture metrics illustrated in FIG. 15 are a percentage of time upright, and an average number of posture transitions per hour. The computing device may determine the average number of posture transitions per hour for one of the illustrated therapy parameter sets by identifying the total number of posture transitions associated with the parameter set and the total amount of time that an IMD or other therapy-delivering medical device was using the parameter set. The computing device may determine the percentage of time upright for one of the parameter sets as the percentage of the total time that the therapy parameter set was in use that the patient was in an upright position, as indicated by the posture-related sensor data from the ADR.

The present application is related to, and incorporates herein by reference, each of the following pending U.S. Patent Applications:
1) U.S. Patent Application entitled "Collecting Sleep Quality Information Via A Medical Device", Ser. No. 10/826,925, filed on Apr. 15, 2004.
2) U.S. Patent Application entitled "Collecting Sleep Quality Information Via A Medical Device", Ser. No. 11/081,811, filed on Mar. 16, 2005.
3) U.S. Patent Application entitled "Collecting Posture Information to Evaluate Therapy", Ser. No. 10/826,926, filed on Apr. 15, 2004.
4) U.S. Patent Application entitled "Collecting Posture Information to Evaluate Therapy", Ser. No. 11/081,872, filed on Mar. 16, 2005.
5) U.S. Patent Application entitled "Detecting Sleep", Ser. No. 10/825,964, filed on Apr. 15, 2004.
6) U.S. Patent Application entitled "Detecting Sleep", Ser. No. 11/081,786, filed on Mar. 16, 2005.
7) U.S. Patent Application entitled "Collecting Activity Information to Evaluate Therapy", Ser. No. 10/825,965, filed on Apr. 15, 2004.
8) U.S. Patent Application entitled "Collecting Activity Information to Evaluate Therapy", Ser. No. 11/081,785, filed on Mar. 16, 2005.
9) U.S. Patent Application entitled "Collecting Activity and Sleep Quality Information via a Medical Device", Ser. No. 10/825,955, filed on Apr. 15, 2004.
10) U.S. Patent Application entitled "Collecting Activity and Sleep Quality Information via a Medical Device", Ser. No. 11/081,857, filed on Mar. 16, 2005.
12) U.S. Patent Application entitled "Controlling Therapy Based on Sleep Quality", Ser. No. 10,825,953, filed on Apr. 15, 2004.
13) U.S. Patent Application entitled "Controlling Therapy Based on Sleep Quality", Ser. No. 11/081,155, filed on Mar. 16, 2005.
14) U.S. Patent Application entitled "Sensitivity Analysis for Selecting Therapy Parameter Sets", Ser. No. 11/081,873, filed Mar. 16, 2005.
15) U.S. Patent Application entitled "Collecting Posture and Activity Information to Evaluate Therapy", Ser. No. 11/106,051, filed Apr. 14, 2005.

16) U.S. Provisional Application entitled "Correlating a Non-Polysomnographic Physiological Parameter Set with Sleep States", Ser. No. 60/686,317, filed Jun. 1, 2005.

An ADR according to the invention may be used in any of the systems described in the incorporated applications to sense any of the physiological parameters described therein. Further, the ADR, a therapy-delivering medical device, specialized programming device, or other computing device may determine values for any of the sleep, activity, or posture metrics described therein. The ADR may be used according to the techniques described in the above-identified applications to sense physiological parameters as instead or in addition to any device described therein as sensing physiological parameters.

As indicated above, movement disorders, such as tremor, Parkinson's disease, multiple sclerosis, and spasticity may affect the overall activity level of a patient. Movement disorders are also characterized by irregular, uncontrolled and generally inappropriate movements, e.g., tremor or shaking, particularly of the limbs. In addition to using the sensors described above to sense the overall activity level of a movement disorder patient, some embodiments of the invention may use such sensors to detect the types of inappropriate movements associated with the movement disorder. For example, accelerometers, piezoelectric crystals, or EMG electrodes located one the trunk or limbs of a patient may be able to detect inappropriate movements such as tremor or shaking.

Embodiments of the invention may periodically determine the level or severity of such movements based on the signals output by such sensors to evaluate the quality of a patient's life or a movement disorder therapy. For example, a processor of such a system may determine a frequency or amount of time that such movements exceeded a threshold for this purpose.

Another activity-related movement disorder symptom that is relatively specific to Parkinson's disease is "gait freeze." Gait freeze may occur when a Parkinson's patient is walking Gait freeze refers to a relatively sudden inability of a Parkinson's patient to take further steps. Gait freeze is believed to result from a neurological failure and, more specifically, a failure in the neurological signaling from the brain to the legs.

Some embodiments of the invention may additionally identify gait freeze events based on the signals output by sensors as discussed above. For example, embodiments may detect a relatively sudden cessation of activity associated with a gait event based on the output of accelerometers, piezoelectric crystals, EMG electrodes, or other sensors that output signals based on footfalls or impacts associated with, for example, walking When experiencing a gait freeze event, a patient may "rock" or "wobble" while standing in place, as if attempting unsuccessfully to move. Some embodiments, may monitor any of the sensors that output signals as a function of posture discussed above, such as a 3-axis accelerometer, to detect the minor, rhythmic changes in posture associated with rocking or wobbling. Such embodiments may detect a gait freeze event as when it occurs based on one or more of the posture or activity sensors. Some embodiments may confirm that a relatively sudden cessation of activity is in fact a gait freeze event based on rocking or wobbling indicated by posture sensors.

Some embodiments may detect a gait freeze prior to onset. For example, the sensors may include EMG or EEG electrodes, and a processor may detect a gait freeze prior to onset based on irregular EMG or EEG activity. EMG signals, as an example, demonstrate irregularity just prior to a freezing episode, and a processor may detect this irregularity as being different from the EMG signals typically associated with walking In other words, a walking patient may exhibit normal EMG pattern in the legs, which may be contrasted with EMG activity and timing changes that precede freezing.

In general, EMG signals from right and left leg muscles include a regularly alternating rhythm pattern that characterizes normal gait. When the "timing" of the pattern fails, there is no longer a regular rhythm, and a gait freeze may result. Accordingly, a processor may detect irregularity, variability, or asymmetry, e.g., within and between right and left leg muscles, in one or more EMG signals, and may detect an oncoming gait freeze prior to occurrence based on the detection. In some embodiments, the processor may compare the EMG signals to one or more thresholds to detect gait freeze. Comparison to a threshold may, for example, indicate an absolute value or increase in irregularity, variability, asymmetry that exceeds a threshold, indicating an oncoming gait freeze. In some embodiments, thresholds may be determined based on EMG signal measurements made when the patient is walking normally.

Whether or not gait freeze is detected prior to or during occurrence, embodiments be used may evaluate quality of life or therapy based on the gait freeze, e.g., total number of gait freeze events for the therapy parameter set, or an average number of gait freeze events over a period of time.

Systems according to the invention may include any of a variety of medical devices that deliver any of a variety of therapies to treat movement disorders, such as DBS, cortical stimulation, or one or more drugs. Baclofen, which may or may not be intrathecally delivered, is an example of a drug that may be delivered to treat movement disorders. Systems may use the techniques of the invention described above to associate any of the above-described sleep quality or activity metrics with therapies or therapy parameter sets for delivery of such therapies. In this manner, such systems may allow a user to evaluate the extent to which a therapy or therapy parameter set is alleviating the movement disorder by evaluating the extent to which the therapy parameter set improves the sleep quality, general activity level, inappropriate activity level, or number of gait freezes experienced by the patient.

Further, many of the ailments and symptoms described above, including movement disorders and chronic pain, may affect the gait of a patient. More particularly, such symptoms and ailments may result in, as examples, an arrhythmic, asymmetric (left leg versus right leg), or unusually variable gait, or a gait with relative short stride lengths. Systems according to the invention may use sensors discussed above that output signals as a function of activity, and particularly as a function of footfalls or impacts, to monitor gait. For example, a processor of such a system may periodically determine a value for asymmetry, variability, or stride length of gait, and use such values to evaluate quality of life, progression of a disease or symptom, or a therapy delivered to treat the symptom Various embodiments of the invention have been described. However, one of ordinary skill will appreciate that various modifications may be made to the described embodiments without departing from the scope of the invention. For example, the invention is not limited to divisions or attributions of functionality described above. Any one or more of an ADR, therapy-delivering medical device, specialized programming device, computing device, or other device may perform the any of techniques of the invention, either alone or in combination.

The techniques described in this disclosure may be implemented in hardware, software, firmware or any combination thereof. For example, various aspects of the techniques may be implemented within one or more microprocessors, digital signal processors (DSPs), application specific integrated circuits (ASICs), field programmable logic arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry, which may be located within one or more devices.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions are executed to support one or more aspects of the functionality described in this disclosure. These and other embodiments are within the scope of the following claims.

The invention claimed is:

1. An external wearable ambulatory data recorder comprising:
    a housing;
    a sensor that generates a signal as a function of posture of a patient that wears the data recorder within the housing;
    a memory within the housing;
    a processor within the housing that receives the signal from the sensor, and stores posture data within the memory for the patient based on the signal;
    an element removably attached to the data recorder, wherein the processor calibrates the sensor in response to removal of the element,
    wherein to calibrate the sensor in response to the removal of the element, the processor identifies an initial value of the signal in response to the removal of the element and associates the initial value with a predetermined posture,
    wherein the posture data corresponds to values of the signal correlated to the initial value of the signal associated with the predetermined posture; and
    an adhesive, wherein the element comprises a removable layer attached to the adhesive, and
    wherein the adhesive is configured to attach the housing to the patient.

2. The data recorder of claim 1,
    further comprising a switch within the housing,
    wherein removal of the element actuates the switch to power on the data recorder, and
    wherein the processor calibrates the sensor in response to the power on of the data recorder.

3. The data recorder of claim 1, wherein the element comprises a magnet.

4. The data recorder of claim 1, wherein the removable layer includes a magnet.

5. The data recorder of claim 1, further comprising a patch that contains the housing and includes the adhesive as a layer.

6. The data recorder of claim 1, wherein the sensor comprises an accelerometer within the housing.

7. The data recorder of claim 1,
    wherein the sensor comprises a plurality of orthogonally aligned accelerometers within the housing, each of the accelerometers generating a signal as a function of posture of the patient, and
    wherein the processor receives the plurality of signals, and stores posture data within the memory for the patient based on the signals.

8. The data recorder of claim 1, further comprising a plurality of sensors that sense a plurality of physiological parameters of the patient, wherein the plurality of sensors are located at least one of on or within the housing.

9. The data recorder of claim 8, wherein the plurality of sensors comprises at least one electrode formed on the housing.

10. The data recorder of claim 8, wherein the plurality of sensors sense at least one of activity, heart activity, brain activity, muscle activity, respiration, temperature, blood oxygen saturation, blood pressure, blood flow, partial pressure of oxygen within blood, partial pressure of oxygen within cerebrospinal fluid, tissue oxygenation, or galvanic skin response of the patient.

11. The data recorder of claim 8, wherein of the processor records at least one of an activity level, a posture, an electrocardiogram, an electroencephalogram, an electromyogram, a heart rate, a heart rate variability, a respiration rate, or a respiration rate variability for the patient within the memory.

12. The data recorder of claim 1, wherein the housing is waterproof.

13. The data recorder of claim 1, wherein a thickness of the housing is less than approximately 1.5 centimeters.

14. The data recorder of claim 1, wherein a volume of the housing is less than approximately 20 cubic centimeters.

* * * * *